(12) United States Patent
Fordham et al.

(10) Patent No.: US 9,551,769 B2
(45) Date of Patent: Jan. 24, 2017

(54) MAGNETIC RESONANCE EXAMINATION OF POROUS SAMPLES

(71) Applicant: SCHLUMBERGER TECHNOLOGY CORPORATION, Sugar Land, TX (US)

(72) Inventors: Edmund J. Fordham, Cambridge (GB); Jonathan Mitchell, Great Cambourne (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 734 days.

(21) Appl. No.: 13/971,515

(22) Filed: Aug. 20, 2013

(65) Prior Publication Data
US 2014/0055134 A1 Feb. 27, 2014

(30) Foreign Application Priority Data
Aug. 23, 2012 (GB) .................................. 1215076.9

(51) Int. Cl.
*G01R 33/48* (2006.01)
*G01N 24/08* (2006.01)
(Continued)

(52) U.S. Cl.
CPC ......... *G01R 33/4818* (2013.01); *G01N 24/081* (2013.01); *G01R 33/50* (2013.01); *G01R 33/56341* (2013.01)

(58) Field of Classification Search
CPC ................ G01R 33/4818; G01R 33/50; G01R 33/56341; G01N 24/081
See application file for complete search history.

(56) References Cited

U.S. PATENT DOCUMENTS 4,868,500 A 9/1989 Baldwin et al.
5,351,525 A 10/1994 Ragazzini et al.
(Continued)

FOREIGN PATENT DOCUMENTS

GB 2489205 A 9/2012
WO 2007003218 A1 1/2007
WO 2010003236 A1 1/2010

OTHER PUBLICATIONS

Ahr, et al., "Confronting the Carbonate Conundrum", Oilfield Review, 2005, pp. 18-29.
(Continued)

*Primary Examiner* — G. M. Hyder

(57) ABSTRACT

A method of analyzing properties of a porous sample, typically a cylinder of porous rock, comprises centrifuging the sample while it contains at least one liquid, determining the distribution of at least one liquid in the sample by magnetic resonance imaging of the sample, and also determining the distribution of at least one magnetic resonance parameter, where the parameter is one of longitudinal relaxation time $T_1$, transverse relaxation time $T_2$ and diffusion coefficient D. Pore throat sizes can be determined from the distribution of at least one liquid in the sample and pore body sizes can be determined from the distribution of the magnetic resonance parameter enabling determination of a relationship between pore throat sizes and pore body sizes in the sample. This can be a relationship between individual values of pore throat size and an average of body sizes of pores having that individual pore throat size.

17 Claims, 15 Drawing Sheets

(51) Int. Cl.
*G01R 33/50* (2006.01)
*G01R 33/563* (2006.01)

(56) References Cited

U.S. PATENT DOCUMENTS

| | | | |
|---|---|---|---|
| 5,886,525 | A | 3/1999 | Yesinowski et al. |
| 6,178,807 | B1 | 1/2001 | Baldwin et al. |
| 6,229,308 | B1 | 5/2001 | Freedman |
| 6,415,649 | B1 | 7/2002 | Spinler et al. |
| 6,883,702 | B2 | 4/2005 | Hurlimann et al. |
| 7,034,528 | B2 | 4/2006 | Minh et al. |
| 7,053,611 | B2 | 5/2006 | Freedman |
| 7,352,179 | B2 | 4/2008 | Chen et al. |
| 7,388,374 | B2 | 6/2008 | Minh et al. |
| 8,427,145 | B2 | 4/2013 | Mitchell et al. |
| 2006/0116828 | A1* | 6/2006 | Chen ............. G01N 24/08 702/22 |
| 2009/0066335 | A1 | 3/2009 | Fleury et al. |
| 2009/0228249 | A1 | 9/2009 | Green |
| 2010/0297659 | A1 | 11/2010 | Yoo |
| 2011/0050223 | A1 | 3/2011 | Balcom et al. |

OTHER PUBLICATIONS

Allen, et al., "The Practical Application of NMR Logging in Carbonates: 3 Case Studies", SPWLA 42nd Annual Logging Symposium, Houston, Texas, Jun. 17-20, 2001, 14 pages.
Arora, et al., "Single-Well In-Situ Measurement of Residual Oil Saturation After an EOR Chemical Flood", SPE 129069—SPE EOR Conference at Oil & Gas West Asia, Muscat, Oman, Apr. 11-13, 2010, 18 pages.
Balcom, et al., "Single-Point Ramped Imaging with T1 Enhancement (SPRITE)", Journal of Magnetic Resonance A., vol. 123 (1), Nov. 1996, pp. 131-134.
Baldwin, et al., "Capillary-pressure Determinations From NMR Images of Centrifuged Core Plugs: Berea Sandstone", The Log Analyst, vol. 32 (5), 1991, pp. 550-556.
Baldwin, et al., "Detecting Fluid Movement and Isolation in Reservoir Core With Medical NMR Imaging Techniques", SPE 14884—SPE Reservoir Engineering, vol. 4 (2), 1989, pp. 207-212.
Baldwin, et al., "NMR Imaging of Fluid Saturation Distributions in Cores", The Log Analyst, vol. 32 (5), 1991, pp. 536-549.
Bloch, F., "Nuclear Induction", Physical Review, vol. 70 (7 and 8), 1946, pp. 460-474.
Bloembergen, et al., "Relaxation Effects in Nuclear Magnetic Resonance Absorption", Physical Review, vol. 73 (7), Apr. 1, 1948, pp. 679-712.
Brownstein, et al., "Importance of classical diffusion in NMR studies of water in biological cells", Phys. Rev. A., vol. 19, Jun. 1, 1979, pp. 2446-2453.
Callaghan, Paul T., "3.3: Reconstruction in two dimensions", Principles of Nuclear Magnetic Resonance Microscopy, Clarendon, Oxford, 1991, pp. 121-129.
Cano Barrita, et al., "Capillary Pressure Measurement in Petroleum Reservoir Cores with MRI", OTC 19234—Offshore Technology Conference, Houston, Texas, May 5-8, 2008, 11 pages.
Carr, et al., "Effects of Diffusion on Free Procession in Nuclear Magnetic Resonance Experiments", Physical Review, vol. 94 (3), May 1, 1954, pp. 630-638.
Chen, et al., "A magnetic resonance study of pore filling processes during spontaneous imbibition in Berea sandstone", Journal of Chemical Physics, vol. 119 (18), Nov. 8, 2003, pp. 9609-9616.
Chen, et al., "Measurement of rock-core capillary pressure curves using a single-speed centrifuge and one-dimensional magnetic-resonance imaging", The Journal of Chemical Physics, vol. 122 (21), Jun. 1, 2005, pp. 214720-214720-8.
Chen, et al., "The Effect of Gravity Degradation on Low-Speed Centrifuge Capillary Pressure Data", AIChE Journal, vol. 41 (3), Mar. 1995, pp. 469-480.
Chen, et al., "The internal magnetic field distribution, and single exponential magnetic resonance free induction decay, in rocks", Journal of Magnetic Resonance, vol. 175 (2), Aug. 2005, pp. 300-308.
Clerke, et al., "Application of Thomeer hyperbolas to decode the pore systems, facies and reservoir properties of the upper Jurassic Arab D limestone, Ghawar field, Saudi Arabia: A "Rosetta Stone" approach", GeoArabia, vol. 13(4), 2008, pp. 113-160.
Cotts, et al., "Pulsed field gradient stimulated echo methods for improved NMR diffusion measurements in heterogeneous systems", Journal of Magnetic Resonance, vol. 83 (2), Jun. 15, 1989, pp. 252-266.
Emid, et al., "High resolution NMR imaging in solids", Physica B+C, vol. 128 (1), Jan. 1985, pp. 81-83.
Fleury, et al., "Quantitative analysis of diffusional pore coupling from T2-store-T2 NMR experiments", Journal of Colloid and Interface Science, vol. 336 (1), Aug. 1, 2009, pp. 250-259.
Forbes, P., "Simple and Accurate Methods for Converting Centrifuge Data Into Drainage and Imbibition Capillary Pressure Curves", The Log Analyst, vol. 35 (4), 1994, pp. 31-52.
Fordham, et al., "Imaging Multiexponential Relaxation in the (Y1 Loge T1) Plane, with Application to Clay Filtration in Rock Cores", Journal of Magnetic Resonance Series A, vol. 113, 1995, pp. 139-150.
Glover, P., "Chapter 8: Capillary Pressure", Formation Evaluation MSc Course Notes, date unknown, pp. 84-94.
Green, Derrick P., "Capillary PRessure Curves Determined by Direct Measurement of the Saturation using Magnetic Resonance Imaging", CWLS Magazine, vol. 28 (1), 2009, pp. 20-25.
Gullion, et al., "New, compensated Carr-Purcell sequences", Journal of Magnetic Resonance, vol. 89 (3), Oct. 1, 1990, pp. 479-484.
Haacke, "Chapter 9: One-Dimensional Fourier Imaging, k-Space and Gradient Echoes", Magnetic Resonance Imaging—Physical principles and sequence design, John Wiley & Sons, Inc., 1999, pp. 121-129.
Hassler, et al., "Measurement of Capillary Pressures in Small Core Samples", SPE 945114—Transaction of the AIME, vol. 160 (1), 1945, pp. 114-123.
Henning, et al., "RARE Imaging: A Fast Imaging Method for Clinical MR", Magnetic resonance in Medicine, vol. 3, 1986, pp. 823-833.
Hirasaki, et al., "Fluid-Rock Characterization for NMR Well Logging and Special Core Analysis", 1st Annual Report to US Department of Energy DE-FC26-04NT15515, Rice University and University of Houston, Nov. 2005, 154 pages.
Hurlimann, et al., "Quantitative Measurement of Two-Dimensional Distribution Functions of Diffusion and Relaxation in Grossly Inhomogeneous Fields", Journal of Magnetic Resonance vol. 157 (1), 2002, pp. 31-42.
Hurlimann, et al., "The diffusion-spin relaxation time distribution function as an experimental probe to characterize fluid mixtures in porous media", Journal of Chemical Physics, vol. 117, 2002, pp. 10223-10232.
Hurlimann, Martin D., "Effective Gradients in Porous Media Due to Susceptibility Differences", Journal of Magnetic Resonance, vol. 131 (2), Apr. 1998, pp. 232-240.
Kaffanke, et al., "Application of the chirp z-transform to MRI data", Journal of Magnetic Resonance, vol. 178, 2006, pp. 121-128.
Kenyon, et al., "Better Pore-Size Distributions From Stimulated-Echo NMR Lab Measurements Using Magnetic Susceptibility Contrast and Small Encoding Angles", SPWLA 43rd Annual Logging Symposium, Oiso, Japan, Jun. 2-5, 2002, 14 pages.
Leverett, M.C., "Capillary Behavior in Porous Solids", SPE 941152—Transactions of the AIME, vol. 142 (1), 1941, pp. 152-169.
Li, et al., "Quantitative discrimination of water and hydrocarbons in porous media by magnetization prepared centric-scan SPRITE", Journal of Magnetic Resonance, vol. 186 (2), Jun. 2007, pp. 282-292.
Li, et al., "Spin echo SPI methods for quantitative analysis of fluids in porous media", Journal of Magnetic Resonance, vol. 198, 2009, pp. 252-260.

(56) References Cited

OTHER PUBLICATIONS

Marica, et al., "Spatially resolved measurement of rock core porosity", Journal of Magnetic Resonance, vol. 178, 2006, pp. 136-141.

Mastikhin, et al., "Water Content Profiles with a 1D Centric SPRITE Acquisition", Journal of Magnetic Resonance, vol. 156, 2002, pp. 122-130.

McDonald, et al., "Surface relaxation and chemical exchange in hydrating cement pastes: a two-dimensional NMR relaxation study", Phys. Rev. E., vol. 72, Jul. 27, 2005, pp. 011409-1-011409-9.

Meiboom, et al., "Modified SpinEcho Method for Measuring Nuclear Relaxation Times", Review of Scientific Instruments, vol. 29, 1958, pp. 688-691.

Mitchell, et al., "A rapid measurement of T1/T2: The DECPMG sequence", Journal of Magnetic Resonance, vol. 200(2), 2009, pp. 198-206.

Mitchell, et al., "Emulation of petroleum well-logging D-T2 correlations on a standard benchtop spectrometer", Journal of Magnetic Resonance, vol. 212 (2), Oct. 2011, pp. 394-401.

Mitchell, et al., "Obtaining true transverse relaxation time distributions in high-field NMR measurements of saturated porous media: Removing the influence of internal gradients", Journal of Chemical Physics, vol. 132, 2010, pp. 244705-1-244705-10.

Mitchell, et al., "Spatially resolved nuclear magnetic resonance studies of planar samples", Progress in Nuclear Magnetic Resonance Spectroscopy, vol. 48 (4), Jul. 30, 2006, pp. 161-181.

Petrov, et al., "T2 distribution mapping profiles with phase-encode MRI", Journal of Magnetic Resonance, vol. 209 (1), Mar. 2011, pp. 39-46.

Provencher, et al., "A Constrained Regularization Method for Inverting Data Represented by Linear Algebraic or Integral Equations", Computer Physics Communications, vol. 27, 1982, pp. 213-227.

Rauschhuber, Michael T., "Profiling of Relaxation Time and Diffusivity Distributions with Low Field NMR", Presentation to Prous Media Consortium Meeting, Rice University, Houston, Apr. 26, 2011, 140 pages.

Rioux, et al., "An Accurate Nonuniform Fourier Transform for SPRITE Magnetic Resonance Imaging Data", ACM Transactions on Mathematical Software, vol. 33 (3), Aug. 2007, 21 pages.

Ruth, et al., "Measurement and Interpretation of Centrifuge Capillary Pressure Curves—the Sca Survey Data", The Log Analyst, vol. 36 (5), 1995, pp. 21-32.

Song, et al., "T1-T2 Correlation Spectra Obtained Using a Fast Two-Dimensional Laplace", Journal of Magnetic Resonance, vol. 154 (2), 2002, pp. 261-268.

Stejskal, et al., "Spin Diffusion Measurements: Spin Echoes in the Presence of a Time-Dependent Field Gradient", Journal of Chemical Physics, vol. 42, 1965, pp. 288-292.

Sun, et al., "Probing the internal field gradients of porous media", Physical Review E, vol. 65, 2002, pp. 051309-1-051309-7.

Weber, et al., "Comparing Strengths of Surface Interactions for Reactants and Solvents in Porous Catalysts Using Two-Dimensional NMR Relaxation Correlations", Journal of Physical Chemistry C, vol. 113 (16), 2009, pp. 6610-6615.

Lawson, et al., "Solving Least Squares Problems", Prentice-Hall, 1974, 12 pages.

Tikhonov, et al., "Solutions of ill-posed problems", V.H. Winston & Sons, 1977, 258 pages.

* cited by examiner

MAGNETIC RESONANCE EXAMINATION OF POROUS SAMPLES

CROSS-REFERENCE TO RELATED APPLICATION

This application claims priority to British Application No. GB1215076.9 filed Aug. 23, 2012, which is incorporated herein by reference in its entirety.

BACKGROUND

This disclosure relates to the examination of porous samples, which may be porous rock, using nuclear magnetic resonance (NMR). In some embodiments of this invention the samples may be material collected in the course of drilling into subterranean rock formations.

It is conventional practice when drilling through underground rock to drill around a central cylinder of rock which is subsequently detached and brought to the surface as a sample, habitually referred to as a rock core. Once brought to the surface, rock cores or pieces cut from them may be subjected to various measurements and tests. The collection of such samples and their examination may be done in connection with exploration for, or exploitation of, hydrocarbons in underground reservoirs. It is also possible that it may be done in connection with exploration for, or the utilisation or management of, underground water, or in connection with schemes for the storage of captured carbon dioxide.

These tests may relate to the pore space of the sample and liquid therein. One characteristic which may be examined is capillary pressure and it can be desirable to determine a capillary pressure curve for the rock sample. Capillary pressure arises when there is an interface between two immiscible fluids in the pores of porous rock. Commonly both fluids are liquids with one wetting the rock and the other being a non-wetting phase, although it is also possible that one fluid is a gas. Capillary pressure arises because the pores, and more specifically the pore throats, act as capillaries. A pore throat is the narrowest point in the pathway into a pore. This capillary pressure can oppose the displacement of a wetting fluid by a non-wetting fluid and has a magnitude dependant on properties of the fluids and on pore throat size. Where there is a distribution of pore throat sizes there will be a distribution of capillary pressures, with the smallest pore throats giving the largest capillary pressure. A capillary pressure curve is a graph of the saturation of the pore space of the sample, usually expressed as a percentage of the total pore space, plotted against capillary pressure.

Determination of pore throat size distribution or the related parameter of a capillary pressure curve is one approach to characterizing rock properties. Another approach to the characterization of rock is the distribution of pore body size which can be obtained by measurement of the distribution of an NMR parameter: transverse relaxation time $T_2$ Pore throat size and pore body size are of course different although there has been some tendency to assume that a pore body size distribution correlates with the pore throat size distribution and then assume that a curve calculated from a pore body size distribution is an acceptable approximation to a capillary pressure curve.

A number of methods of measurement are commonly used examination of rock samples. Generally these obtain values or distributions of values which are an average for the whole sample under examination.

One well-established method of determining the sizes of pores in a rock is Mercury Injection Capillary Pressure (MICP) or Mercury Porosimetry. This core analysis measurement is widely used in reservoir engineering for Reservoir Rock Typing (RRT) i.e., classification of rocks in a petroleum-bearing formation. The injection of mercury into a dry, evacuated rock at various pressures is measured and the incremental injection volumes at various pressures are used to derive a Pore Size Distribution (PSD) for the rock, where the pore "size" is pore throat size derived from the Washburn equation for a capillary.

Another approach to measurement recognizes that a capillary pressure curve can be established for sample which contains, or is in contact with, two immiscible fluids. Such a curve can be established for a sample where a liquid is being replaced by a gas, usually air (drainage) or where a liquid is replacing gas (imbibition) or where one liquid is replacing another. A known test procedure for obtaining a capillary pressure curve entails centrifuging a liquid-saturated porous sample at various speeds. Liquid drains from pores in the sample when centripetal acceleration overcomes capillary pressure, which can therefore be determined by measuring the amount of liquid which drains from the sample at the various speeds, as originally described in Hassler, G. L., Brunner, E., "Measurement of Capillary Pressure in Small Core Samples", Trans. AIME, 1945, 160, 114-123 also published as Society of Petroleum Engineers paper SPE 945114-G.

It is also known, for the purpose of obtaining a capillary pressure curve, to centrifuge a sample and then use nuclear magnetic resonance (NMR) sometimes termed magnetic resonance imaging (MRI) to measure a liquid saturation profile, i.e., measure the amount of liquid at a plurality of positions along the length of the rock sample.

This has been described in U.S. Pat. No. 4,868,500 for brine which is replaced by air as a centrifuge forces drainage of brine from the rock sample. In U.S. Pat. No. 6,178,807 it has been described for a combination of oil and brine where centrifuging causes one liquid to replace the other within the rock sample. See also Chen and Balcom in Journal of Chemical Physics Vol. 122, 214720 (2005) and the related U.S. Pat. No. 7,352,179.

The extent of pore saturation, i.e., the amount of the liquid in the pores, may be determined from the intensity of the magnetic resonance signal for each position along the length of the rock sample. The spatial position from which resonant nuclei emitted signals may be detected using coils to superimpose a magnetic field gradient onto the main magnetic field, so that the spatial position is "frequency encoded".

The literature has also disclosed techniques in which the spatial position in a rock sample is indicated by the phase of the received signals, so that the spatial position is said to be "phase encoded." An advantage of phase encoded imaging is that each data point is recorded at a fixed time after initial excitation, so any effects arising from relaxation after the initial excitation are the same for the entire sample.

A phase encoded single point imaging (SPI) pulse sequence disclosed by S. Emid and J. H. N. Creyghton, "High-resolution NMR imaging in solids," Physica B & C, Vol. 128(1), pp. 81-83, 1985 may be used for the measurement of saturation profiles in reservoir rock samples. The SPI pulse sequence has been improved by use of small angle radio frequency spin excitation pulses (see B. J. Balcom et al., "Single-point ramped imaging with T1 enhancement (SPRITE)," J. Magn. Reson. Ser. A, Vol. 123(1), pp. 131-134, 1996).

Whilst there is a distinct difference between phase encoded and frequency encoded techniques, as pointed out above, it should also be appreciated that the literature describes a variety of frequency encoded techniques as well as a variety of phase encoded techniques.

SUMMARY

This summary is provided to introduce a selection of concepts that are further described below. This summary is not intended to limit the scope of the subject matter claimed.

Disclosed herein is a method of analysis of properties of a porous sample, which may be rock from a rock core, comprising centrifuging the sample while it contains at least one liquid and using magnetic resonance to examine a distribution of liquid in the rock sample relative to the direction of centripetal acceleration by the centrifuge characterized by also using magnetic resonance to determine a distribution relative to the direction of centripetal acceleration of one or more of the parameters longitudinal relaxation time $T_1$, transverse relaxation time $T_2$ and diffusion coefficient D.

By obtaining a distribution of liquid in the sample and a distribution of one of the magnetic resonance parameters it is possible to obtain more information about a porous sample than is obtained if only a distribution of liquid or only a distribution of one of the magnetic resonance parameters is determined. In a number of embodiments, the magnetic resonance parameter is transverse relaxation time $T_2$ which is a parameter that has also been chosen for acquisition using NMR well logging tools as for instance mentioned in U.S. Pat. No. 6,229,308.

The distribution of liquid in the sample may be used to determine a capillary pressure curve. Values of a magnetic resonance parameter, for instance values of $T_2$ may be used to characterize and distinguish between different parts of the overall porosity of the sample. For example, pores of smaller and larger body sizes may be distinguished from each other by selecting a value of $T_2$ as a boundary between the smaller and larger sizes. It is then possible to combine the determination of distributions of liquid and distributions of $T_2$ and obtain separate capillary pressure curves for liquid in these categories of pores.

Because the distributions of liquid and of magnetic resonance parameter may relate to different characteristics of the pores of the rock they may be utilized for determining relationships between properties. One instance of this is correlation between pore body size and pore throat size.

The determinations of properties of liquid distribution and distribution of magnetic resonance parameter may be carried out in any sequence, or may be carried out concurrently. Observations of magnetic resonance to determine these properties may be carried out with a nuclear magnetic resonance spectrometer which is computer controlled. Observed data may be received by a programmable computer, which may or may not be the controlling computer and calculations of properties and correlations of properties may be performed with a programmable computer which receives the observed data in raw or processed form.

Centrifuging the sample may cause forced drainage of liquid from the sample and/or it may cause forced imbibition. So for example centrifuging may force drainage of brine which is replaced by air entering the sample. In some embodiments centrifuging may be carried out with two liquids, for example to force drainage of oil while part of the sample is in contact with brine so that oil which drains from the sample is replaced by brine.

A number of magnetic resonance techniques are available and may be used for determining the spatial distribution of liquid in the sample and a number of techniques are available and may be used for determining magnetic resonance parameters such as $T_2$. "Phase-encoded" techniques in which phase of the received signals indicates the spatial position from which resonant nuclei emit signals may be used. In some embodiments, however, resonance is observed in a magnetic field with a superimposed magnetic field gradient and the spatial position of from which signals are emitted is "frequency encoded".

The spatial position may be frequency encoded both for determination of the distribution of liquid, and also for the determination of the distribution of a parameter $T_1$, $T_2$ or D. The same magnetic resonance imaging procedure may be used to determine both distributions concurrently.

Nuclear magnetic resonance can observe a number of nuclei but may observe liquid in a rock sample by observation of $^1H$ nuclei (i.e., protons). Such nuclei are abundant in both water and hydrocarbon and so $^1H$ magnetic resonance can observe the distribution of an oil phase or an aqueous phase within a sample when the other fluid present in the sample is air. It is also possible to observe the replacement of one liquid by another, if one liquid is made invisible to magnetic resonance or by using a technique which can distinguish between them.

Embodiments within the present disclosure may be performed with a spectrometer in which the magnetic field (in the absence of any field gradient) does not exceed 1 Tesla and may lie in a range from 0.02 to 0.5 Tesla. A bench top spectrometer may have a magnetic field in this range. At such a range of magnetic field the values of $T_2$ tend to be higher than at a greater magnetic field, which facilitates obtaining results with contrast between $T_2$ values of different liquid phases.

Data may be obtained for spatial positions which are at least 0.1 mm apart, for instance from 0.1 to 2 mm from one position to the next. This spatial resolution may be lower than is customary for medical MRI but is adequate for the study of rock samples and allows the time between the spin and echo pulse and times between successive echo pulses to be kept short, enhancing the speed of data acquisition and reducing the effect of relaxation ($T^*_2$) brought about by field inhomogeneity.

It may be convenient to apply the present methods to samples cut from a rock core, such as a cylindrical sample having a length in the range 4 cm to 10 cm which is placed in line with a magnetic field gradient in the spectrometer and having a diameter in a range of 1.5 cm to 5 cm. Of course if the length of a cylindrical sample is in line with the magnetic field gradient, the cross-section will be transverse to the field gradient.

An NMR spectrometer to carry out the method of this invention may be connected to, or incorporate, a controlling computer to control its operation and to receive and process data.

DETAILED DESCRIPTION

Apparatus

Figure 1:
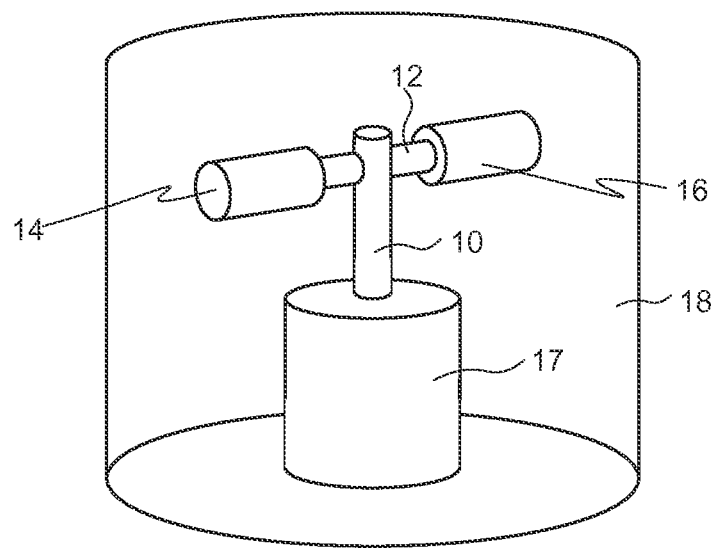
FIG. 1 schematically illustrates a centrifuge.

FIG. 1 schematically illustrates a centrifuge for a porous rock sample. It has a shaft 10 carrying the rotor arm 12 with a sample holder 14 at one end and a counterweight 16 at the other end. The shaft is turned by a motor 17 and all of the parts are located within an outer container 18.

Figure 2:
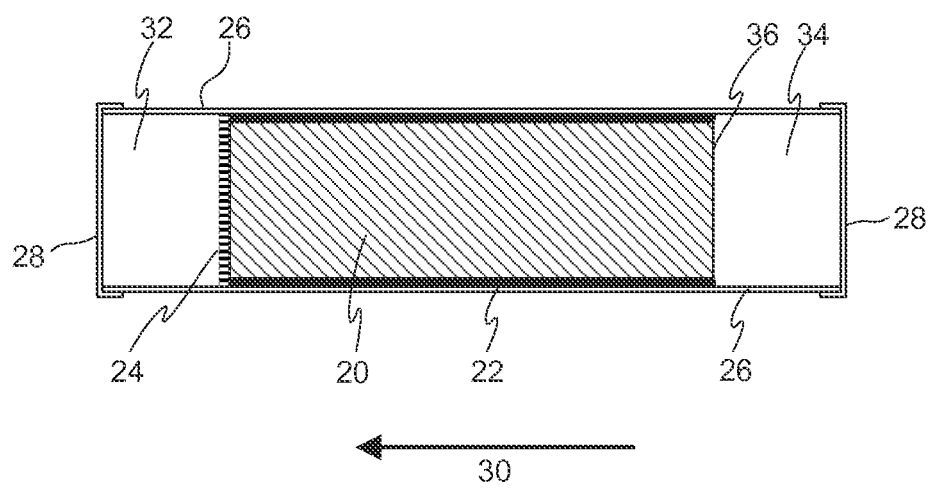
FIG. 2 is a diagrammatic cross section of a rock sample in a centrifuge.

As schematically shown by FIG. 2, the sample holder 14 is constructed to accommodate a cylindrical rock sample 20 in a fixed position, with its curved surface surrounded by an impermeable sheath 22 so that fluid in the rock sample can enter and leave through its end faces. The outer end of the sample abuts an apertured wall 24. The holder has a cylindrical body 26 of non-magnetic material and removable end caps 28.

The rotation of the centrifuge subjects the cylindrical rock sample 20 to centripetal acceleration (inaccurately but commonly termed centrifugal force) in the axial direction indicated by arrow 30. During rotation, liquid in the sample can be forced out through the apertured wall 24 into the space 32 at the radially outer end of the sample holder. This is referred to as forced drainage. If desired by the experimenter, liquid can be placed in the space 34 at the radially inner end, to be drawn into the sample through its end face 36 as the centrifuge rotates. This is referred to as forced imbibition.

The rotational speed of the centrifuge determines the magnitude of the centripetal acceleration, but the acceleration also depends on the radial distance from the axis of shaft 10, so that the magnitude of centripetal acceleration varies along the length of the sample 20. Movement of liquid in the sample in response to this centripetal acceleration is opposed by capillary forces retaining the liquid in the pores of the rock and also by viscosity of the liquid limiting the rate at which it can flow. During centrifuging, liquid will drain from a pore if centripetal acceleration overcomes capillary pressure at that pore. It is normal to run the centrifuge for a sufficiently long time that liquid in the sample 20 reaches an equilibrium distribution.

At equilibrium, capillary pressure $P_c$ is defined as the difference between the pressures of wetting $P_{wetting}$ and non-wetting $P_{nonwetting}$ fluids in contact with a curved surface such as the wall of a pore:

$$P_c = P_{nonwetting} - P_{wetting} \qquad (1)$$

and is related to the radius R of a cylindrical pore throat by:

$$P_c = \frac{2\gamma \cos\varphi}{R}, \qquad (2)$$

where $\gamma$ is the interfacial tension between the two fluids and $\phi$ is the contact angle. This capillary pressure is thus a property of the rock, the fluids and the pore throat size. The capillary pressure acts to retain liquid in place and opposes cenrifugal acceleration which urges liquid to drain from pores.

However, in the present context it is useful to use "capillary pressure" to refer to a value of the capillary pressure parameter which is matched by the pressure applied to the fluid by centripetal acceleration, which is dependant on angular velocity and radial distance from the centrifuge axis.

This value of capillary pressure varies along the length of the sample. The rate of change of capillary pressure along the length of a sample is given by $$\frac{dP_c}{dz} = \Delta\rho a_c \qquad (4)$$

where $\Delta\rho$ is the density difference between the wetting and non-wetting fluids and where the centrifugal acceleration $a_c$ associated with angular velocity $\omega$ at a radius r relative to the centrifuge axis is given by $a_c = -\omega^2 r$. Therefore, assuming the capillary pressure at the outlet face of the sample is zero, i.e., there is no opposition to centripetal acceleration at the outlet face of the sample is zero, the capillary pressure as a function of radius is given by $$P_c(r) = \frac{1}{2}\Delta\rho\omega^2(r_2^2 - r^2) \qquad (5)$$

where $r_2$ is the radial distance from the centrifuge axis to the radially outer face of the sample.

If the liquid which drains is measured by volume or weight, the result is an average for the entire sample, so that use of the above relationships to obtain a capillary pressure curve requires assumptions and approximations. However, as has been disclosed in the literature, these can be avoided by magnetic resonance imaging which allows direct determination of the spatially resolved saturation state of the sample.

Obtaining MRI Profile

An MRI profile is acquired in the direction of the centrifugal acceleration. This profile is the magnetic resonance signal observed for each of a sequence of small pixels along the axial direction of the sample. If one fluid is a liquid containing nuclei which display magnetic resonance while the other fluid gives negligible NMR signal (for instance if it is a gas) the magnitude of the signal is directly proportional to the amount of liquid within the pixel width and can be expressed as a percentage of total saturation. Each pixel is associated with a different centrifugal acceleration even though the centrifuge is only operating at a single speed and the capillary pressure at each pixel can be calculated using equation (5) above. Plotting percentage saturation against capillary pressure for all the pixels gives the capillary pressure curve. It is theoretically possible that the complete capillary pressure curve $P_c(r)$ can be determined as a function of saturation from a single measurement.

For this to be achieved, the MRI data need to cover a saturation profile with a range of percentage saturation values along the rock sample. The duration and centrifuge speed to achieve this will vary with porosity and permeability of the rock sample as well as with properties of the liquid(s) in the sample and may have to be found by experiment. Estimation of a suitable speed may be assisted by the scaling law introduced to petroleum engineering by Leverett in "Capillary behavior in porous solids," *Trans. AIME*, Vol. 142, pp. 152-169 (1941) whereby capillary pressure is non-dimensionalised according to the so-called "Leverett J-function" in which J is a function of water saturation $S_w$ $$J(S_w) = \frac{p_c(S_w)\sqrt{k/\phi}}{\gamma \cos\theta} \tag{6}$$

where $\sqrt{(k/\phi)}$ is a characteristic value serving as a simple proxy for pore throat size based upon permeability k and porosity $\phi$ which are macroscopic parameters that are routinely measured.

The value of J provides a convenient means of scaling the gross effects of interfacial tension $\gamma$, contact angle $\theta$, and pore size, and describes a position on an ideal, "dimensionless" capillary pressure characteristic. Porous media with geometrically similar microgeometries will be expected to have identical $J(S_w)$ characteristics.

In the context of a centrifuge capillary pressure determination, the maximum capillary pressure (reached at the inner face of the sample) is given by equation (5) where $r=r_1$. The scaled maximum is given by $$J^{(max)} = \frac{\omega^2 \Delta \rho (r_2^2 - r_1^2)}{2\gamma \cos\theta} \sqrt{\frac{k}{\phi}} \tag{7}$$

This provides a means of estimating the centrifugation speed $\omega$ to be used for a particular rock, with porosity $\phi$ and permeability k, in a centrifuge of given dimensions and with a liquid of surface tension $\sigma$ and contact angle $\theta$ against the rock minerals. An actual speed to be used can be determined according to a re-arrangement of equation (7):

$$\omega^2 = \frac{2J^{(max)}\gamma \cos\theta}{\Delta \rho (r_2^2 - r_1^2)} \sqrt{\frac{\phi}{k}} \tag{8}$$

In practice, the MR profiles may be acquired for a few Leverett J-function numbers to determine the full capillary pressure curve.

There is more than one way to construct and operate a magnetic resonance spectrometer to measure the amount of fluid at different spatial positions. Apparatus for one approach in which position is frequency encoded is shown diagrammatically by FIG. 3. The sample holder 14 containing the sample 20 is placed within a radiofrequency coil 40 (which may be wound around a non-magnetic tube, not shown) and positioned between two main magnets 42, 44 which may be permanent magnets and which provide a homogenous magnetic field in the direction $B_0$ transverse to the axis of the sample 20.

The radiofrequency coil 40 is used to apply radiofrequency signals to the sample 20 within the sample holder 14 and also to act as an antenna receiving signals from the sample. If desired the coil 40 could be replaced with separate transmitter and receiver coils which might be wound one on top of the other with the same central axis. A pair of gradient coils 46, 48 is located between the magnets 42, 44 and these can be energised to create a magnetic field gradient superimposed on the main magnetic field such that the magnetic field strength increases along the length of the sample.

The gradient coils 46, 48 and the radiofrequency coil 40 are connected to operating and controlling electronics system 52 which includes a programmable computer 53 and can energise the gradient coils, energise the coil 40 to transmit radio frequency signals and also record signals received by the coil 40 when it is acting as an antenna. The computer 53 may carry out computations with the recorded signal data, or the recorded data may be output in a batch to a general purpose programmable computer 55 for further processing and the display and output of results.

When the gradient coils 46, 48 are energised to create the field gradient, the resonant frequency of nuclei in the magnetic field varies along the length of the sample 20 and so the resonant frequency of nuclei indicates position along the linear dimension parallel to the axis of the sample 20. A spectrometer of this general character was disclosed in U.S. Pat. No. 4,868,500.

The spectrometer may be operated to apply an excitation pulse of radiofrequency energy, without the gradient coils 46, 48 energised, so as to excite resonant nuclei throughout the sample 20 while the magnetic field is uniform, followed by energising the gradient coils and receiving echoes of the excitation pulse over a range of frequencies. The spatial position along the length of the sample is then encoded by the frequency of the received signals. The amplitude at each frequency will be proportional to the number of nuclei which emit the echo signal and so a plot of signal amplitude against frequency will provide the distribution of emitting $^1H$ nuclei along the dimension parallel to the sample axis.

A different approach to using magnetic resonance to measure the amount of fluid at different spatial positions is to use phase encoding, which may be as implemented using the SPRITE protocol as described by Chen and Balcom "Measurement of rock-core capillary pressure curves using a single-speed centrifuge and one-dimensional magnetic-resonance imaging," J. Chem. Phys., vol. 122, p. 214720 (2005) and also in the related U.S. Pat. No. 7,352,179.

Distribution of Another Magnetic Resonance Parameter

Besides measuring the amount of fluid at different spatial positions, magnetic resonance is also used to determine one or more magnetic resonance parameters at a range of spatial positions along the sample length. These parameters may be longitudinal or transverse relaxation times, customarily designated $T_1$ and $T_2$ respectively and also diffusion coefficient D.

These parameters could be measured by a phase encoded or a frequency encoded method. Both have been reported in the literature although not in association with centrifuging of samples. For example Fordham et al., "Imaging multiexponential relaxation in the (y, $\log_e T_1$) plane, with application to clay filtration in rock cores," J. Magn. Reson. A, Vol. 113, pp. 139-150, (1995) have described a frequency encoded method for mapping rock samples for the $T_1$ parameter. Petrov et al., Journal of Magnetic Resonance Vol. 209, pp. 39-46 (2011) described phase encoded mapping of $T_2$ by two methods, one of which was referred to as CPMG-prepared SPRITE and the other referred to as spin-echo SPI.

We have found that there are advantages in determining the spatial distribution of a magnetic resonance parameter, notably $T_2$, by means of a frequency encoded method comprising:

placing the sample in a magnetic field;

applying a 90° radiofrequency pulse to the sample;

superimposing a magnetic field gradient on the magnetic field (and optionally observing the radiofrequency emitted from the sample over a range of frequencies);

observing echo signals by a sequence of steps which are removing the superimposed magnetic field gradient and applying a 180° refocusing pulse, then again superimposing a magnetic field gradient on the magnetic field and observing the radiofrequency emitted from the sample over a range of frequencies while the magnetic field gradient is applied;

repeating that sequence many times to observe repeated echo signals; and calculating values correlating radiofrequency signal strength with at least one of $T_1$, $T_2$ and D at positions distributed within the sample.

The repeated observation of echo signals as stated above may be a considerable number of repetitions, possibly more than a thousand repetitions.

Using this frequency encoded method for determining spatial distribution of one of the magnetic resonance parameters, the data for a one-dimensional profile of $T_1$, $T_2$ or D values along a line can be acquired in a single scan consisting of an excitation pulse, repeated refocusing pulses and observation of radiofrequency emission in the intervals between these pulses. Because data can be acquired in a single scan, the data acquisition time is short.

Figure 3:
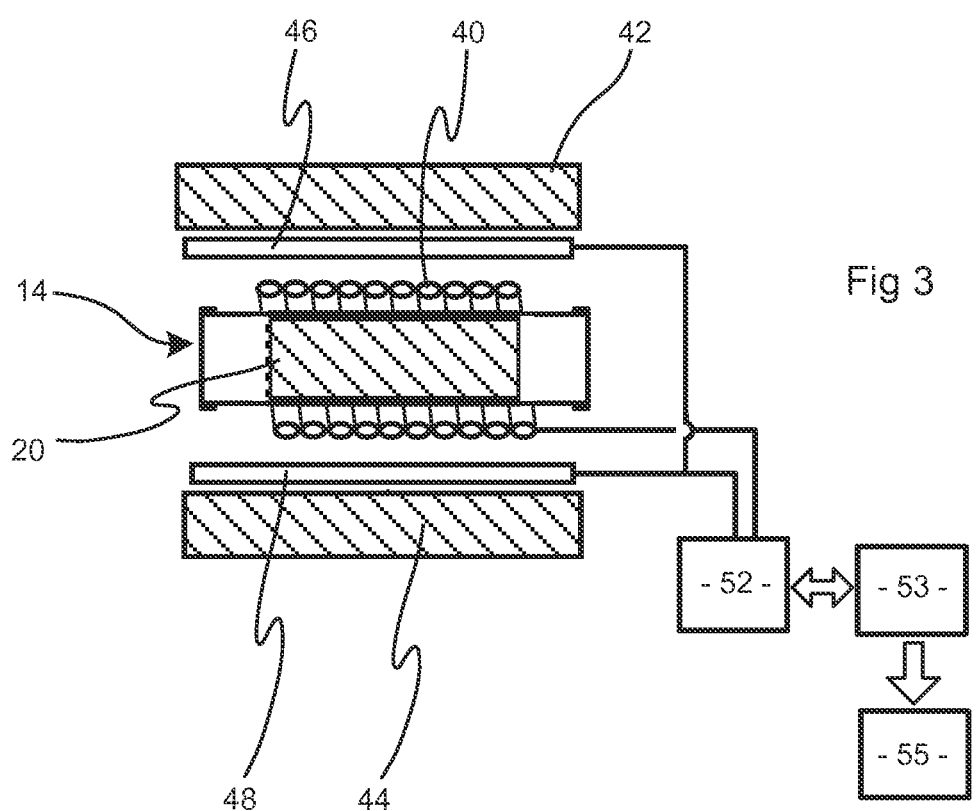
FIG. 3 schematically illustrates an NMR spectrometer.

Frequency encoded determination of spatial distribution of $T_1$, $T_2$ and/or D may be carried out using an NMR spectrometer with the parts illustrated by FIG. 3. A pulse sequence which may be employed in the determination of $T_2$ distribution is shown diagrammatically by FIG. 4. With the sample holder 14 containing sample 20 in place within coil 40 as shown in FIG. 3 and with the gradient coils 46, 48 de-energized so that the magnetic field is uniform, a 90° radio frequency pulse 60 is applied by means of the coil 40 to excite the spins. Current is then applied to the gradient coils 46, 48 to superimpose a magnetic field gradient of amplitude $G_y$ on the main magnetic field for a duration t/2. During this time the field gradient remains constant and the radio frequency coil 40 is used as an antenna to receive the spin signal from the sample 20.

Next the coils 46, 48 are de-energised and a 180° refocusing radio frequency pulse 62 is applied a time $\tau$ after the 90° radio frequency pulse 60 so as to form a spin echo. Current is again applied to the gradient coils 46, 48 to superimpose a magnetic field gradient of amplitude $G_y$ on the main magnetic field for a duration t while the echo signal is received by the coil 40.

The steps of de-energising the gradient coils 46, 48 and then applying a refocusing pulse 62 and reenergizing the coils 46, 48 while an echo signal is acquired are repeated n times to form and receive a train of n spin echoes. Each echo is acquired in the presence of the magnetic field gradient of amplitude $G_y$ applied for a time t. The interval between refocusing pulses is $2\tau$. This echo time $2\tau$ may be set to the minimum possible in order to provide an accurate $T_2$ measurement.

As is common for MRI the received signals are Fourier transformed into reciprocal space (k-space). When the magnetic field is applied for a time t the observed frequency range spanned in k-space is given by $$\pm k_{max} = \pm \frac{\gamma G_y t}{2\pi} \qquad (9)$$

where $\gamma$ is the gyromagnetic ratio of the nuclear spins, e.g., spins of $^1$H nuclei, and $k_{max}$ is the maximum deviation from the resonant frequency $f_0$. Each point in k-space will have a width defined by $$\Delta k = \frac{\gamma}{2\pi} G_y \Delta t \qquad (10)$$

where $\Delta t$ is the dwell time (the time over which the continuous analogue radio frequency signal is summed to form a discrete digital data point). If the time t between echoes is subdivided into m data points, $\Delta t = t/m$. This minimum to which the echo time $2\tau$ can be set will be determined by the parameters of the profile acquisition (specifically $G_y$, t, m and $\Delta t$). Experimentally, setting m=64 and $\Delta t$=10 microseconds it is possible to achieve $2\tau$=1 millisecond on current commercial bench-top spectrometers. This is limited predominantly by gradient performance and also storage capacity since m×n complex data points need to be acquired.

Processing of the data is divided into the following steps. First, each of the n echoes is Fourier transformed. As part of this process it is desirable to include a first order phase shift. This is achieved automatically by barrel shifting the k-space echo such that the maximum signal intensity corresponds to k=0. The echoes are then stacked to form a 2D data set such that each spatial position has an associated $T_2$ decay. A zero$^{th}$ order phase shift is applied at this stage to rotate the majority of the complex signal into the real channel. The imaginary channel data may be used to estimate the signal-to-noise ratio (SNR) of the data but otherwise may not be needed. The real channel data may be stored for further processing without storing imaginary channel data. A numerical inversion method is then applied individually to each exponential decay to form a distribution of $T_2$ relaxation time. Each exponential decay is described by the first kind Fredholm integral equation $$\frac{s(y; t_E)}{s(0)} = \int_{-\infty}^{\infty} f(\log_{10} T_2; y) k_0(T_2, t_E) d(\log_{10} T_2) \qquad (11)$$

where $k_0 = \exp\{-t_E/T_2\}$ is the model function describing the expected signal decay. Here $f(\log_{10}T_2)$ is proportional to the volume of fluid having relaxation time $T_2$, within some range d $\log_{10}T_2$. Appropriate numerical inversion methods for estimating $f(\log_{10}T_2)$ include non-negative least squares (NNLS) fitting as taught by C. L. Lawson and R. J. Hanson, "Solving Least Squares Problems" Prentice-Hall, 1974 and Tikhonov regularisation as taught by A. N. Tikhonov and V. Y. Arsenin, "Solutions of ill-posed problems" V. H. Winston & Sons, (1977) as implemented in the popular CONTIN program, see S. W. Provencher, "A constrained regularization method for inverting data represented by linear algebraic or integral equations," Comput. Phys. Commun., Vol. 27, pp. 213-227, (1982).

Figure 4:
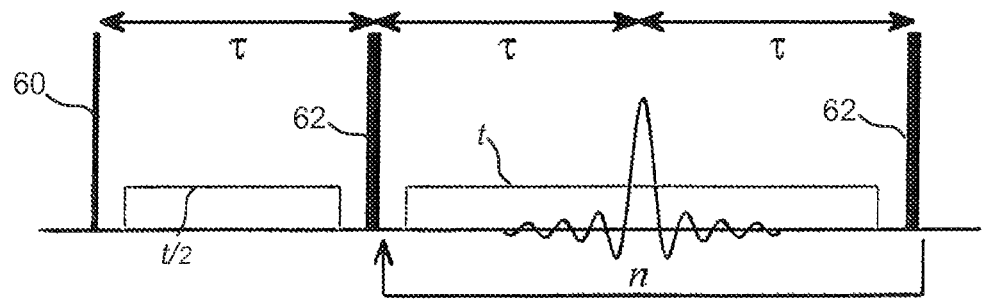
FIGS. 4, 5 and 6 are diagrams of pulse sequences used in an NMR spectrometer.
Figure 5:
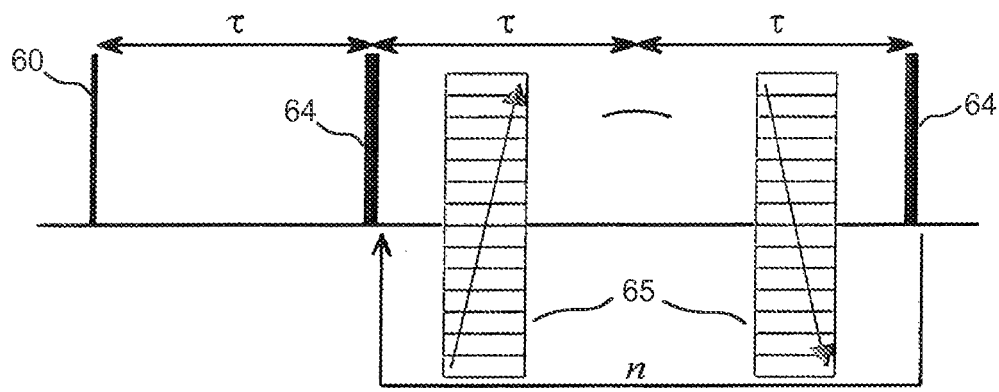

FIG. 5 shows the pulse sequence for a phase encoded procedure. Here too a 90° radio frequency pulse 60 is applied by means of coil 40 to excite the spins. A 180° refocusing radio frequency pulse 64 is applied after time τ and repeated at intervals of 2τ. As indicated at 65, phase encoding magnetic field gradients of progressively varying amplitude ranging across $\pm G_{max}$ are applied for a time $t_p$ before and after each echo acquisition, as taught by Balcom et al. in "Single-Point Ramped Imaging with $T_1$ Enhancement (SPRITE)" Journal of Magnetic Resonance, Series A vol 123, pages 131-134 (1996). The minimum echo time here is approximately the same as for the frequency encoded method shown by FIG. 4.

Figure 6:
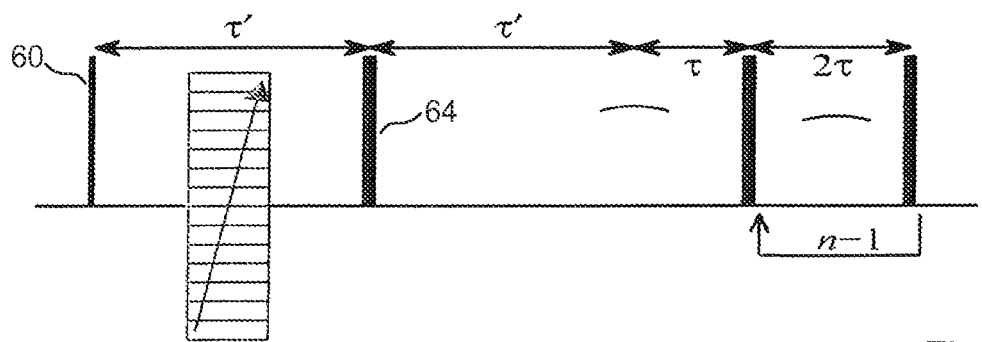

FIG. 6 shows the pulse sequence for a different phase encoded procedure. This is based on Li et al., "Spin echo SPI methods for quantitative analysis of fluids in porous media," J. Magn. Reson., vol. 198, pp. 252-260 (2009) and also. WO 2010/003236 A1. Again a 90° radio frequency pulse 60 is applied by means of coil 40 to excite the spins. A 180° refocusing radio frequency pulse 64 is applied after time τ' and during this interval between the excitation pulse and the first refocusing pulse a single phase encoding magnetic field gradient of progressively varying amplitude ranging across $\pm G_{max}$ and duration $t_p$ is applied.

In phase encoding profiles, each point in k-space is described by $$k_y = \frac{1}{2\gamma G_y t_p}, \quad (12)$$

and the field of view (FOV) will be $$FOV = \frac{m}{\gamma G_{max} t_p}. \quad (13)$$

while the image resolution is given by $$\Delta y = \frac{\pi}{\gamma G_{max} t_p} \quad (14)$$

The processing of the $T_2$ map obtained from the phase encoding methods is achieved in the same way as described above for the frequency encoded method.

Figure 7:
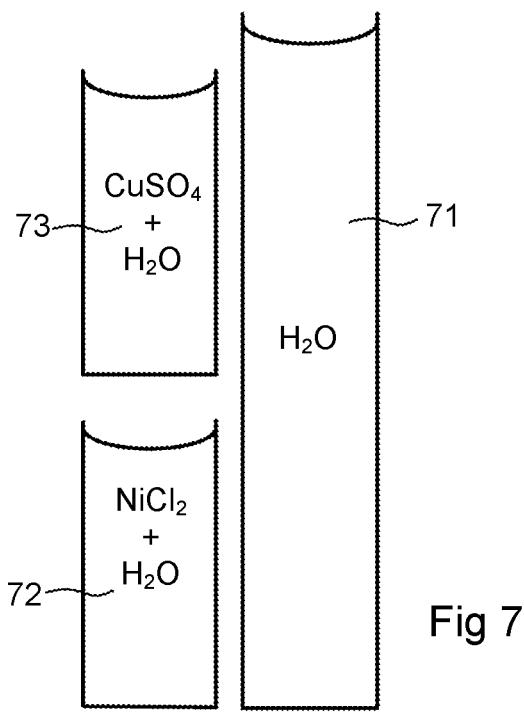
FIG. 7 shows an imaging phantom provided by three tubes of liquid.

A comparative test was carried out using an imaging phantom illustrated by FIG. 7. This consisted of three tubes, 71, 72, 73 arranged as shown. The tube 71 contained deionised water, and tubes 72 and 73 contained solutions of paramagnetic ions to give different $T_2$ relaxation times. These were

| Tube | Contained | $T_2$ |
|---|---|---|
| 71 | Deionised water | 2 seconds |
| 72 | NiCl$_2$ solution | 0.16 seconds |
| 73 | CuSO$_4$ solution | 0.04 seconds |

$T_2$ maps of the imaging phantom were made using each of the methods and pulse sequences described above with reference to FIGS. 4 to 6. The resulting $T_2$ maps are somewhat schematically illustrated by FIGS. 8 to 10. Each of these was a map of magnetic resonance signal intensity over a range of values of $T_2$ and for each pixel along the longitudinal of the MR profile (the vertical direction as shown in FIG. 7). The original maps showed signal intensity as a grey scale, but here the areas of high signal intensity are outlined and indicated 74. A plot of magnetic resonance signal intensity against T2 (in seconds) extends along the base of each of these maps and a plot of signal intensity against longitudinal position is at the right hand side.

Figure 8:
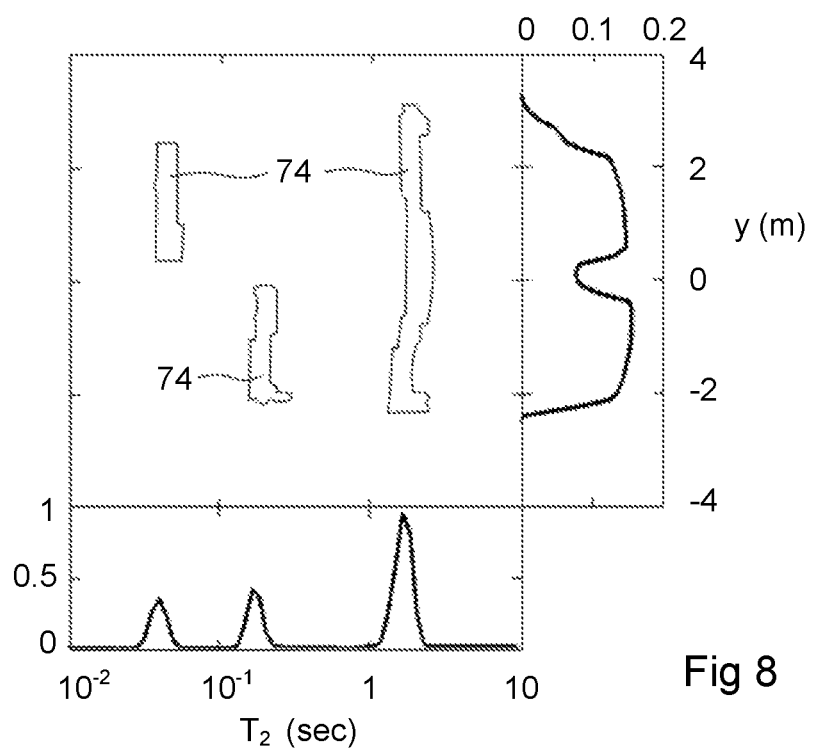
FIGS. 8, 9 and 10 are maps of magnetic resonance signal against position and $T_2$ observed for the imaging phantom.

FIG. 8 shows that the frequency encoding method described with reference to FIG. 4 provided the best determination of $T_2$ distribution. It was noted that the $T_2$ of the deionised water was reduced from 2 seconds to 1.8 seconds due to diffusion in the presence of the imaging gradients. However, this will not be an issue in most petrophysical sample studies as the pore structure of the rock limits the path length available for free diffusion. Additionally, any such attenuation could if so desired be calculated and removed from the $T_2$ fit using the method described in Mitchell et al., "Obtaining true transverse relaxation time distributions in high-field NMR measurements of saturated porous media: removing the influence of internal gradients," J. Chem. Phys., vol. 132, p. 244705, 2010.

The image profile is distorted due to the convolution of $T_2^*$ attenuation (i.e., the echo envelope) with the k-space signal. An additional processing step can be included to remove this distortion since the $T_2^*$ relaxation, determinable by a simple free induction decay (FID) experiment, is approximately mono-exponential in liquid saturated rocks as taught by Chen et al., "The internal magnetic field distribution, and single exponential magnetic resonance free induction decay, in rocks," J. Magn. Reson., vol. 175, pp. 300-308, 2005.

Figure 9:
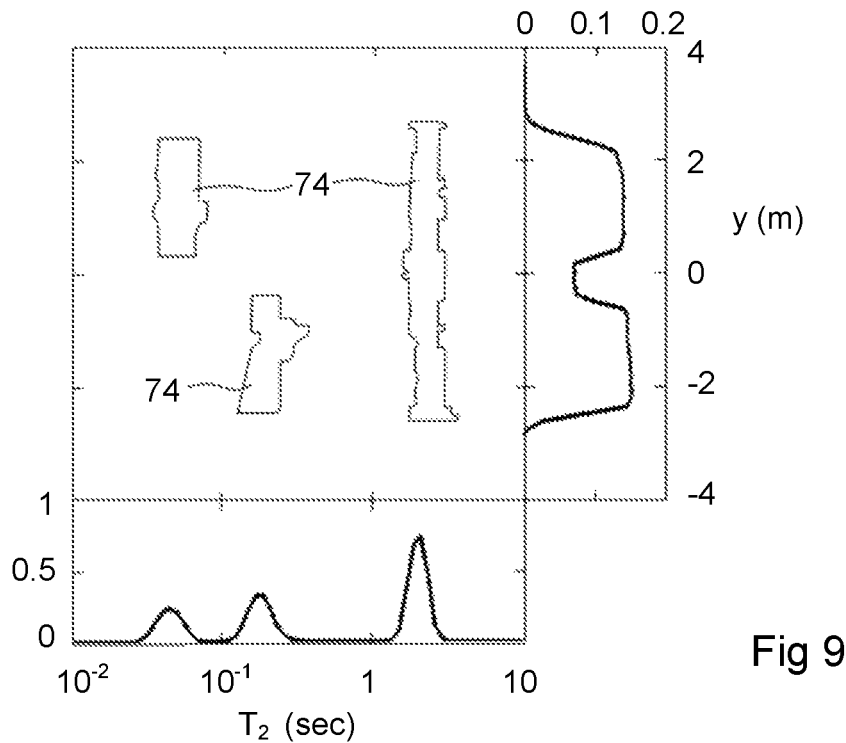
Figure 10:
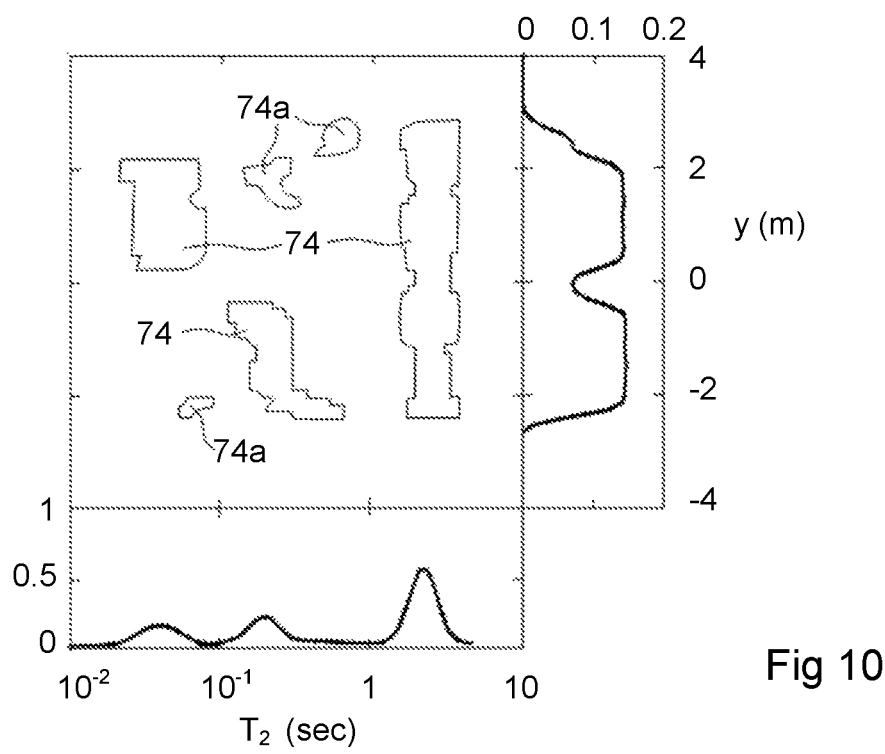

FIGS. 9 and 10 show that the $T_2$ distributions were less well defined when using the phase encoded spin-echo method of FIG. 5 and the modified spin-echo SPI method of FIG. 6. The map from the method of FIG. 6, shown here by FIG. 10 included areas of intermediate signal intensity 74a.

Example of Testing

A number of tests were carried out applying methods as above to samples which were rock samples of cylindrical form, 38 mm diameter and 50 mm length. The samples were initially saturated with an aqueous brine and centrifuging expelled brine which was replaced by air (ie forced drainage).

Figure 11:
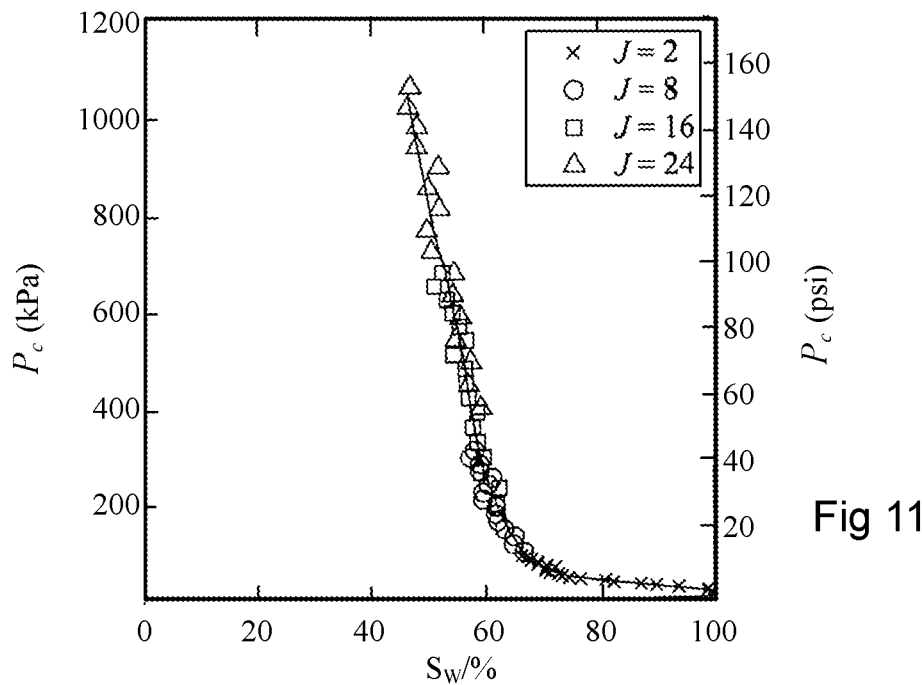
FIG. 11 is a capillary pressure curve for Estaillades limestone.
Figure 12:
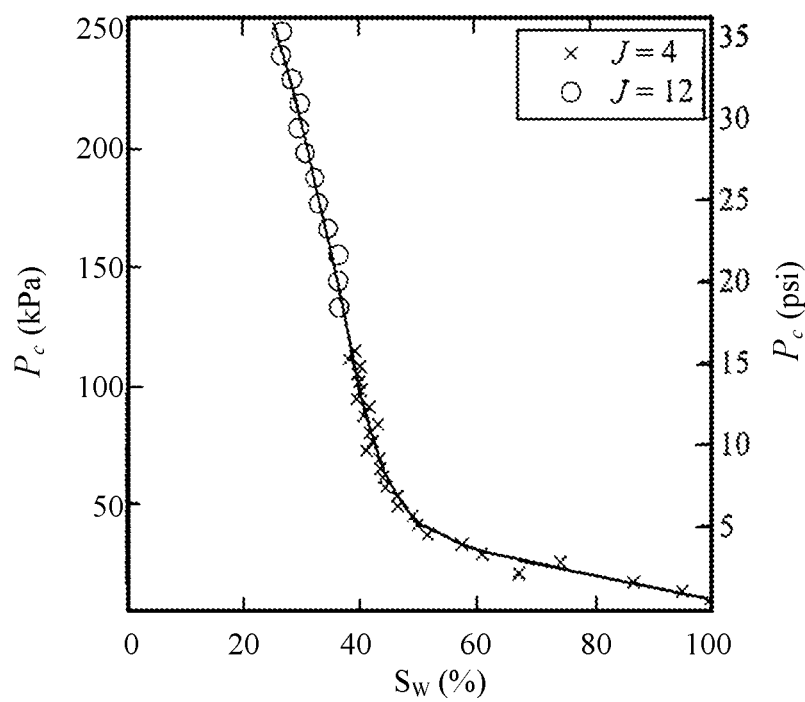
FIG. 12 is a capillary pressure curve for Berea sandstone.

FIGS. 11 and 12 show capillary pressure curves for samples which are Estaillades limestone and Berea sandstone respectively. Distribution of liquid in a sample was obtained using the frequency encoded magnetic resonance method as described above to obtain magnetic resonance profiles along the direction of the sample axis after centrifuging at several speeds corresponding to Leverett J values as indicated.

Figure 13:
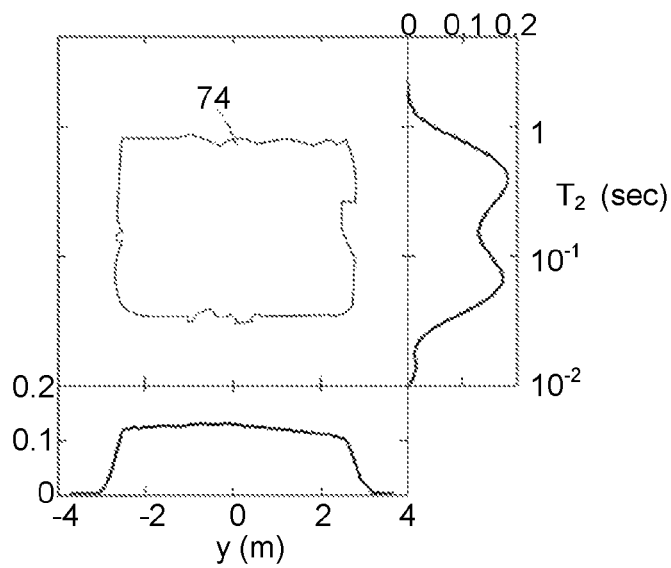
FIGS. 13 to 15 are maps of magnetic resonance signal against position and $T_2$ observed in Estaillades limestone.
Figure 14:
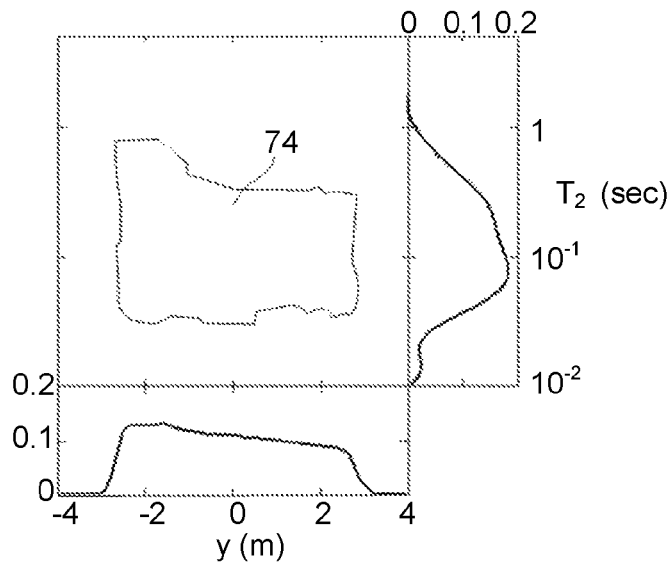
Figure 15:
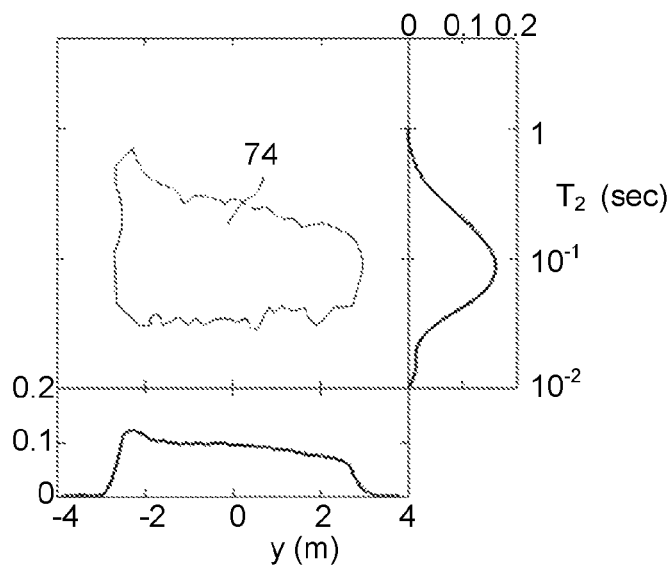

Magnetic resonance was also used to determine distribution of $T_2$ values when the Estaillades limestone sample was centrifuged. FIG. 13 schematically illustrates a map of signal intensity plotted for $T_2$ and for position along the direction of the sample axis (the y direction) of the brine-saturated sample before centrifuging. The original map showed signal intensity as a grey scale, but here the region of the map where signal intensity is high is indicated as an outlined area 74. FIGS. 14 and 15 are corresponding maps after centrifuging at Leverett J values of 0.5 and 2. These maps shown as FIGS. 13 to 15 are in principle similar to those shown as FIGS. 8 to 10 but are shown with $T_2$ on the vertical axis and a plot of $T_2$ against signal intensity at the right hand side. It is apparent from these observations of $T_2$ distribution that this rock has a bi-modal pore size distribution. Brine in macro pores is associated with longer $T_2$ values and brine in micro-pores is associated with shorter $T_2$ values. The $T_2$ maps reveal the spatial distribution of brine in the macropores and micropores. As the sample drains, it can be seen from the $T_2$ maps that the large pores empty first, leaving only the microporosity saturated at J=2.

Using the observation of $T_2$ it becomes possible to obtain a capillary pressure curve for the macroporosity only. This may be done by selecting, for each pixel of the MR profile, the part of the resonance signal which is associated with $T_2$ values longer than a chosen limit (in this example 0.1 sec) and hence associated with macropores. This part of the signal is then used to determine a value of capillary pressure at the pixel, calculated using equation (5) above and plotted as a capillary pressure curve.

Figure 16:
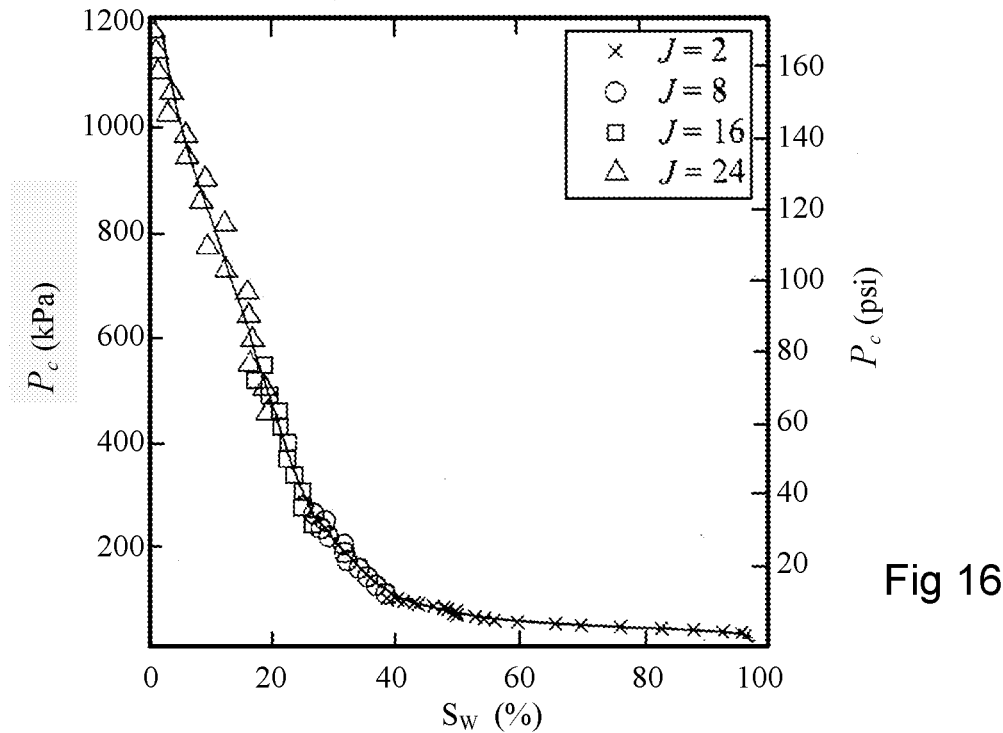
FIG. 16 is a capillary pressure curve for the macropores of the Estaillades limestone sample used for FIG. 11.

Such a curve for the macroporosity in the Estaillades limestone is shown in FIG. 16. It will be appreciated that FIG. 11 and FIG. 16 are both capillary pressure curves for the same sample. The distinction between them is that FIG. 11 is a curve for the whole porosity of the sample while FIG. 16 is a curve for a portion of the porosity: namely the larger pores delimited by a $T_2$ value longer than 0.1 sec. FIG. 11 shows about 50% of the total porosity to be "irreducible" porosity comprising pores which are too small to be drained by centrifuging. This irreducible porosity is not apparent in FIG. 16 because the curve in FIG. 16 relates to a portion of the porosity.

Body Size Distribution from $T_2$ Distribution

One purpose for determination of the distribution of $T_2$ is that $T_2$ is related to pore body size. It is well-recognized from the physics of NMR for fluids in pores (see for example K. R. Brownstein and C. E. Tan, "Importance of classical diffusion in NMR studies of water in biological cells," Phys. Rev. A, vol. 19, pp. 2446-2453 (1979) that $T_2$ indicates a pore body size, or strictly, a Volume to Surface Ratio V/S, rather than the pore throat sizes to which capillary pressure is sensitive. The relevant volume to surface ratio is that of the pore that is approximately independent, to diffusing molecules, of its neighbours. The basic model of NMR logging interpretation is thus that $T_2$ values are proportional to S/V, through a parameter (with dimensions of velocity) called the surface relaxivity $\rho_2$:

$$\frac{1}{T_2} = \rho_2 \frac{S}{V} \tag{15}$$

We may identify a "spherical-equivalent" pore diameter $d_b$ as 6 V/S so that $$\frac{1}{T_2} = \rho_2 \frac{S}{V} = \rho_2 \frac{6}{d_b} \tag{16}$$

and equivalently, the very simple interpretation of $T_2$ in terms of pore body size:

$$d_b = 6\rho_2 T_2 \tag{17}$$

Distinction Between Pore Throat and Body Sizes

As will be explained in more detail below, the concepts disclosed here have applicability to relationships between pore body sizes and pore throat sizes. The importance of distinguishing between these characteristics is shown by the following comparison.

As mentioned above it is well known to use NMR to obtain a measurement of $T_2$ distribution for the whole of a sample. The integral form of the $T_2$-distribution $$F(\log_{10} T_2) = \int_{-\infty}^{\log_{10} T_2} f(\log_{10} T_2) d(\log_{10} T_2) / \int_{-\infty}^{\infty} f(\log_{10} T_2) d(\log_{10} T_2) \tag{18}$$

suitably normalized between 0 and 1, is sometimes regarded as equivalent to Saturation $S_w$, as a function of pore size $d_b = 6\rho_2 T_2$, given in (17) above, because it gives the volume fraction of all pores smaller than a particular size $d_b$:

$$F(\log_{10} T_2) = S_w (d_b 6\rho_2 T_2) \tag{19}$$

This relationship can be interpreted in terms of capillary pressure on the basis that the small pores as defined by the equation 19 above are expected to remain filled, and larger pores to be drained, when centrifuging subjects them to a local pressure $p_c$ related to $d_t$ by the Washburn equation $$d_t = 4\frac{\gamma \cos\theta}{p_c} \tag{20}$$

and making the unjustified assumption that pore size $d_b$ and pore throat size $d_t$ are the same.

A "pseudo-capillary pressure" $p_c^{(pseudo)}$ for any value of $T_2$ may then be defined as $$p_c^{(pseudo)} = \frac{2\gamma \cos\theta}{3\rho_2 T_2} \tag{21}$$

Then $F(\log_{10} T_2)$ may be recast as $S_w(p_c^{(pseudo)})$:

$$F(\log_{10} T_2) = S_w(d_b = 6\rho_2 T_2) = S_w\left(T_2 = \frac{2\gamma\cos\theta}{6\rho_2 p_c^{(pseudo)}}\right) \tag{22}$$

Then, solving for $p_c^{(pseudo)}(S_w)$, the "pseudo-capillary pressure" characteristic may be derived.

Figure 17:
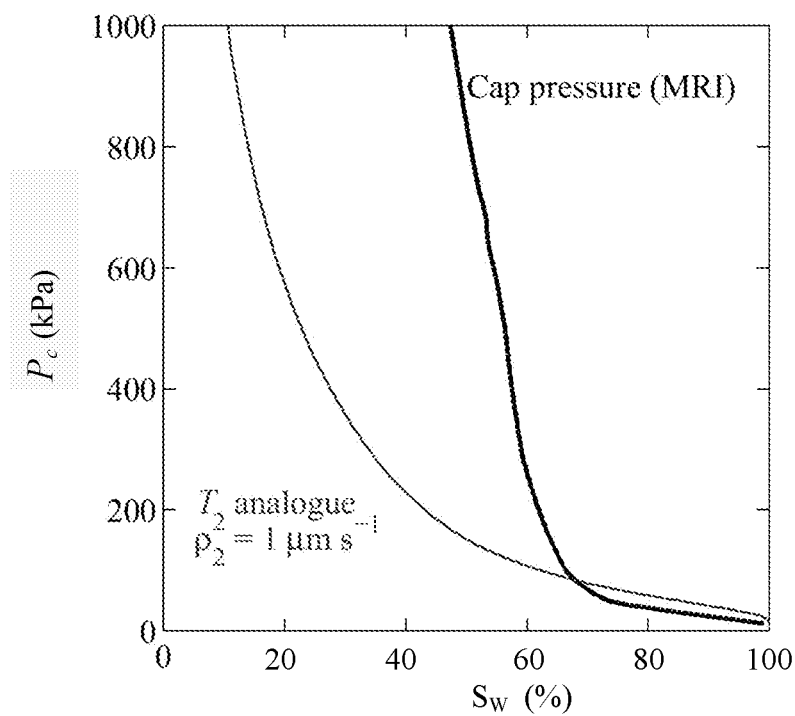
FIG. 17 shows a curve calculated from $T_2$ distribution of a sample and a capillary pressure curve obtained by magnetic resonance imaging of the same sample.

FIG. 17 shows a pseudo capillary pressure curve derived in this way from $T_2$ distribution for a sample of Estaillades limestone and also a capillary pressure curve derived from magnetic resonance imaging of the same sample in the manner described above. It can be seen that the two curves are close together at saturations of 70% and above but diverge very considerably at lower saturation percentages.

Relation Between Body and Throat Sizes

The present inventors have appreciated that by using NMR to obtain distributions of $T_2$ as well as distribution of liquid within the sample, it is possible to utilize the NMR data to provide more information about the relation between pore volume and pore throat sizes. Two possibilities for interpretation of NMR data will be described below. It is envisaged that investigation of body and throat size relations will be carried out using a liquid as one fluid within the sample and a gas (which gives negligible NMR signal) as the other fluid. The gas may simply be air from the atmosphere which replaces liquid as centrifuging causes drainage from a sample which is initially liquid-saturated.

Pore sizes in a sample and likewise the associated values of $T_2$ are distributed over a range. When a liquid saturated sample is centrifuged, causing partial drainage, it is normally observed that the distribution of $T_2$ changes. Typically there is some correlation between body size and throat size such that the larger pores drain before smaller ones and the mean of $T_2$ moves towards shorter values associated with small pores.

Figure 18:
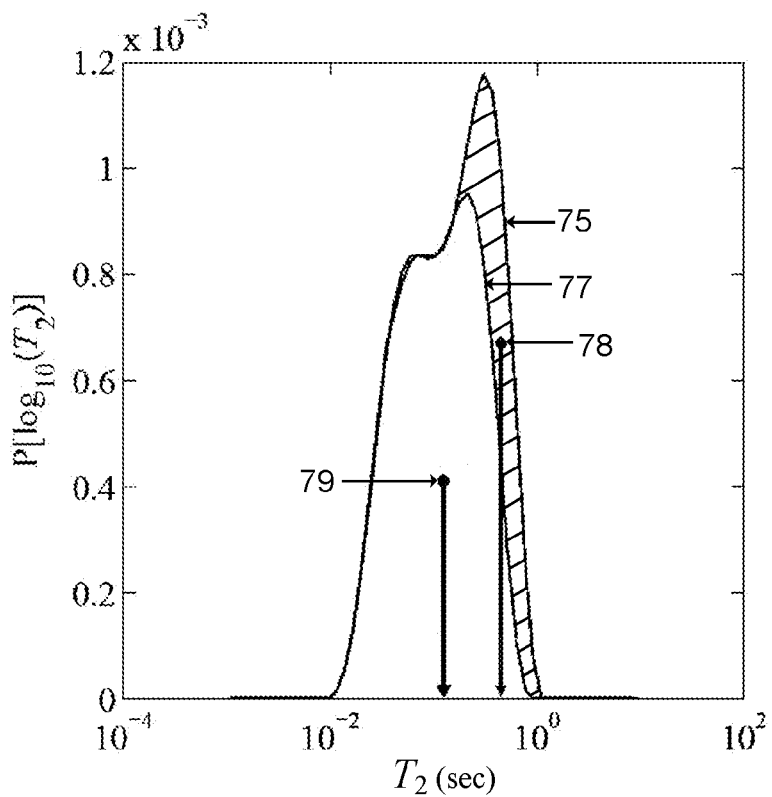
FIG. 18 is a plot showing $T_2$ distribution for a sample of Estaillades limestone when fully saturated with brine and after partial drainage.

This is illustrated by FIG. 18 which is a plot showing the distribution of $T_2$ for a sample of Estaillades limestone when fully saturated with brine and after partial drainage. The outline 75 is for the fully saturated sample, the outline 77 is that for the partially saturated sample. At the left-hand edge the two outlines coincide. The area within outline 77 corresponds to pores which remain saturated. The hatched area between the two outlines corresponds to pores which have already drained. Average $T_2$ (indicated 78) for the pores that have already drained, is larger than average $T_2$ (indicated 79) for the pores which have not drained.

As already mentioned, each pixel in the MRI profile corresponds to a portion of the sample at a certain radial distance from the centrifuge axis. The pressure imposed by centrifuging will cause drainage of pores in that pixel with throat size larger than a certain value. That boundary value of throat size corresponds to the smallest pore throats which drain in that pixel. They may be referred to as the pores which have "just drained" because pores with throats of the same size in an adjacent pixel nearer to the centrifuge axis will not drain.

Interpretation 1: Relating Throat Size to an Average Body Size

It is customary in petrophysics to refer to logarithmic mean $T_2$ written as $T_{2LM}$ although this is more correctly a geometric mean. If $\log_{10} T_2$ is denoted by x, i.e., $x = \log_{10} T_2$, and the distribution of $\log_{10} T_2$ is $f(x)$, then $$\log_{10} T_{2LM} = \langle x \rangle = \int_{-\infty}^{\infty} x f(x) dx \qquad (23)$$

where $\langle x \rangle$ is the standard arithmetic mean of x. Consequently, $T_{2LM} = 10^{\langle x \rangle}$.

One possibility for correlating information about throat and body sizes is to determine the pore throat size $d_t$ which is the boundary value (maximum throat size) for draining of pores at a specific capillary pressure $p_c$ using the Washburn equation $$d_t = 4 \frac{\gamma \cos\theta}{p_c} \qquad (20)$$

and correlate this with a logarithmic mean pore body size for pores which remain saturated, calculated as $$\langle d_{b,sat} \rangle = 6 \rho_2 T_{2LM}^{(i)} = 6 \rho_2 10^{\langle x \rangle_i} \qquad (24)$$

Figure 22:
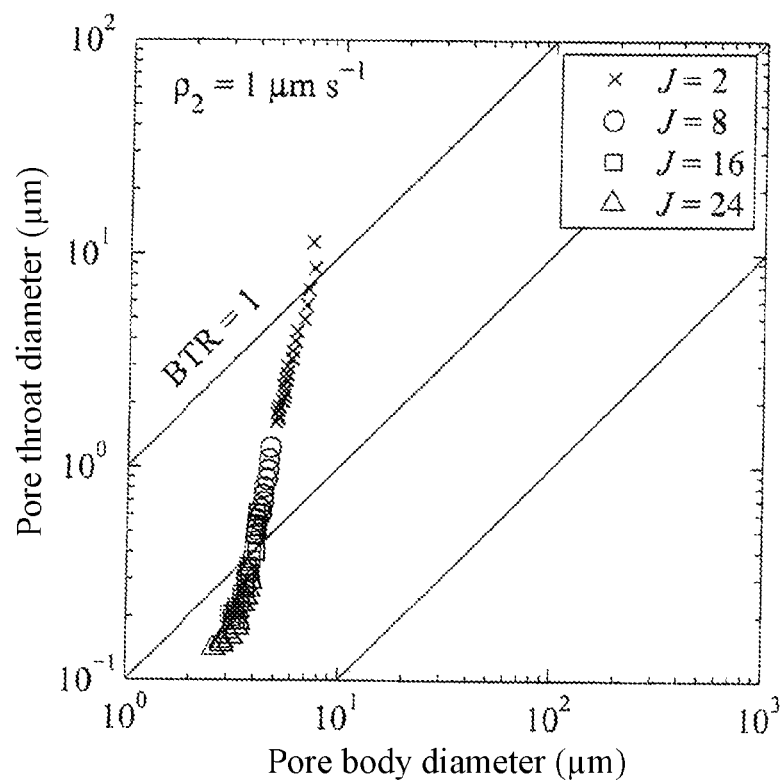
FIG. 22 is a plot of pore throat diameter against an average of pore body size which remains saturated, in Estaillades limestone.
Figure 24:
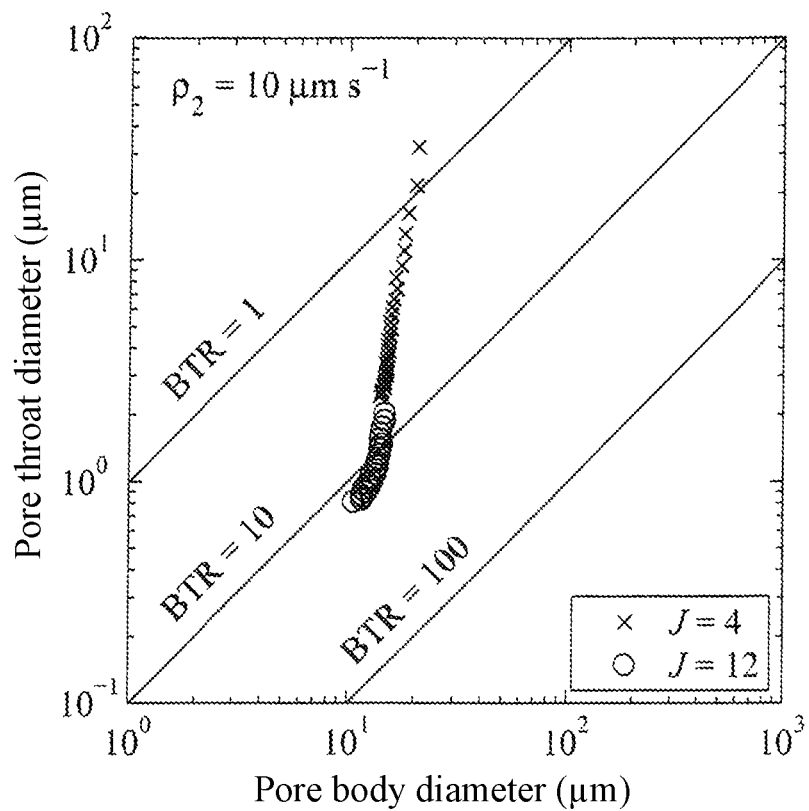
FIG. 24 is a plot of pore throat diameter against an average of pore body size which remains saturated, in Berea sandstone.

This is simple to calculate, on a pixel-by-pixel basis, for each pixel in the MRI profile, and has good signal to noise ratio. It must be interpreted carefully however since in any given pixel, the throat size is a size boundary at the capillary pressure $p_c$ whereas the body size estimate, however, is a volume-weighted average body size of those pores that remain saturated, i.e., have "not yet drained." Thus for any given throat size, it is a ratio of that throat size to the average body size of the set of pores which remain saturated and therefore have that throat size as their maximum throat size. FIGS. 22 and 24 illustrate this interpretation of data. They are plots of "average saturated pore body size" $\langle d_{b,sat} \rangle$ from equation 24 against "throat size" $d_t$ from equation 13 for Estaillades limestone and Berea sandstone respectively.

Interpretation 2: Relating Associated Throat and Body Sizes

A second possibility, which gives a more direct correlation of body and throat sizes, uses a new method of processing the data as will now be explained.

In our new method of calculation from a $T_2$ distribution we compare the distributions at different places along the length of the sample which have different states of saturation after centrifuging. Using the variable i to denote progressives states of drainage, if $f_0(x)$ (for the wholly saturated state i=0) has been properly normalized to 1, then the saturation $S_w$ in state i is given simply by $$S_w^{(i)} = \int_{-\infty}^{\infty} f_i(x) dx \qquad (25)$$

We define the logarithmic average relaxation time over the difference between two distributions where i=1 and i=2 as:

$$\langle x \rangle_{12} = \int_{-\infty}^{\infty} x((f_1(x) - f_2(x)) dx / \int_{-\infty}^{\infty} ((f_1(x) - f_2(x)) dx \qquad (26)$$

The definition is applicable generally, but we employ it when the change in saturation between the two states is relatively small, as for example between near-neighbour pixels in a MRI image profile of a centrifuged sample.

This presumes that $f_0(x)$ is normalised to unity for the fully saturated state (i=0). If $f_i(x)$ for the partially saturated states are consistent with $f_0(x)$, then the integrals $$\int_0^{\infty} f_i(x) dx$$

will all be less than unity; in fact they are the saturations:

$$S_w^{(i)} = \int_{-\infty}^{\infty} f_i(x) dx \qquad (27)$$

Also, because the distributions are no longer normalized to unity, the logarithmic mean of each distribution taken separately requires normalization for the logarithmic mean $T_2$ (interpreted as a mean pore size for pores still saturated) to be correct:

$$\langle x \rangle_i = \int_{-\infty}^{\infty} x f_i(x) dx \Big/ \int_{-\infty}^{\infty} f_i(x) dx \qquad (28)$$

We compare the saturation states for pixels in the MR profile which are near neighbours. These are pixels i and (i+n) in the sequence of pixels where n is a small integer. The near neighbours have a finite difference in saturation, for which $\langle x \rangle_{i,i-n}$ may be calculated. As in any differential measurement, the effect of experimental errors is readily amplified. The value of n can be adjusted, or averages over adjacent pixels may be taken, so as to obtain sufficient contrast in the $T_2$ distributions for the calculation of $\langle x \rangle_{i,i-n}$ not to be unduly influenced by experimental error. Then the expression $$\langle d_b \rangle = 6 \rho_2 T_{2LM}^{(i,i-n)} = 6 \rho_2 10^{\langle x \rangle_{i,i-n}} \qquad (29)$$

provides a measure of the volume-weighted average body size of those pores that have "just drained," i.e., have drained in the pixel(s) being considered but would not have drained under the slightly lower centripetal acceleration in the neighbor pixel(s) taken as comparison. This directly correlates with the throat size, determined by the local capillary pressure, of pores that have "just drained" i.e., have throat sizes adjacent the boundary for draining under the local capillary pressure. We calculate $\langle x \rangle_{i,i-n}$ from pixels which include or are adjacent to the pixel for a given capillary pressure, and then the body size (an average over all pores "just drained") and throat size (determined from $p_c$) are for the same pores, viz. those that are at the drainage boundary and have "just drained." Not only is this measure of body to throat ratio obtained from a single experimental situation, but the pore throat and body sizes are known to go together, by the circumstances of the measurement. Furthermore all pore body sizes associated with a given throat size and capillary pressure are included in the volume-weighted average. For example, very poorly-connected macropores draining only at a high capillary pressure may drain at the same capillary pressure as micropores and both will be included in an average value of body size for pores draining at that capillary pressure.

Figure 19:
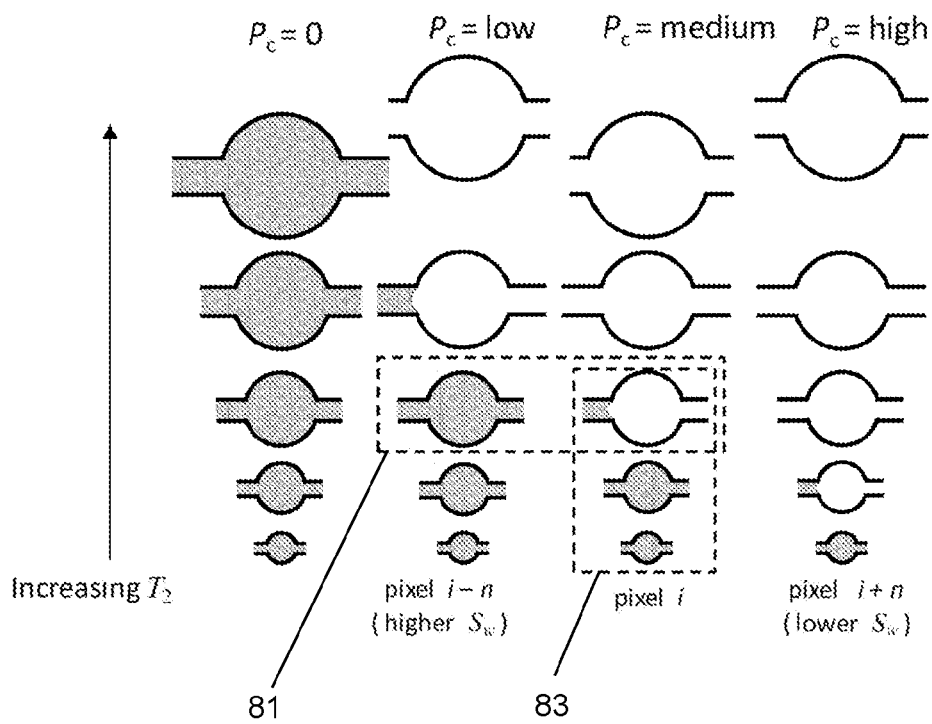
FIGS. 19, 20 and 21 are diagrams of pores and pore throats illustrating drainage while centrifuging.
Figure 20:
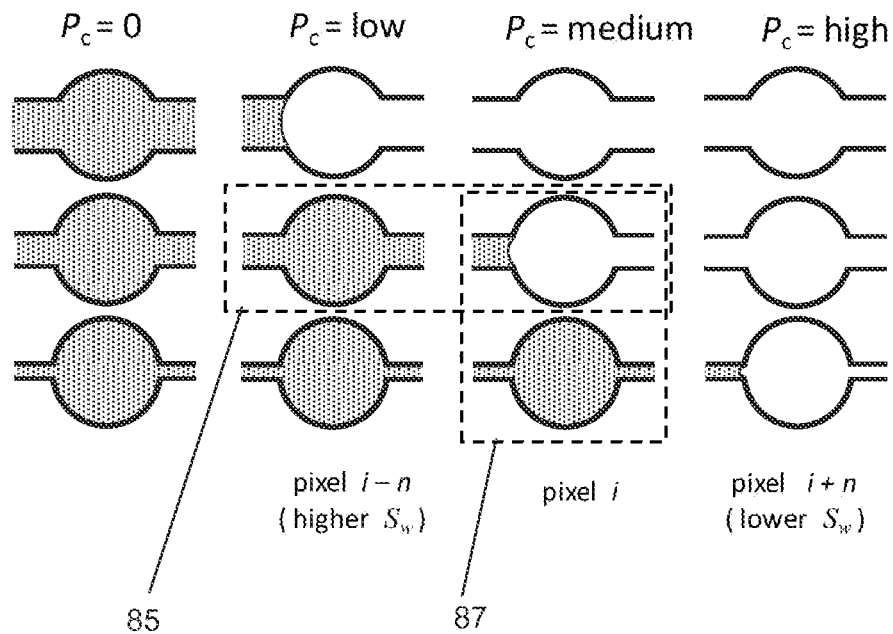
Figure 21:
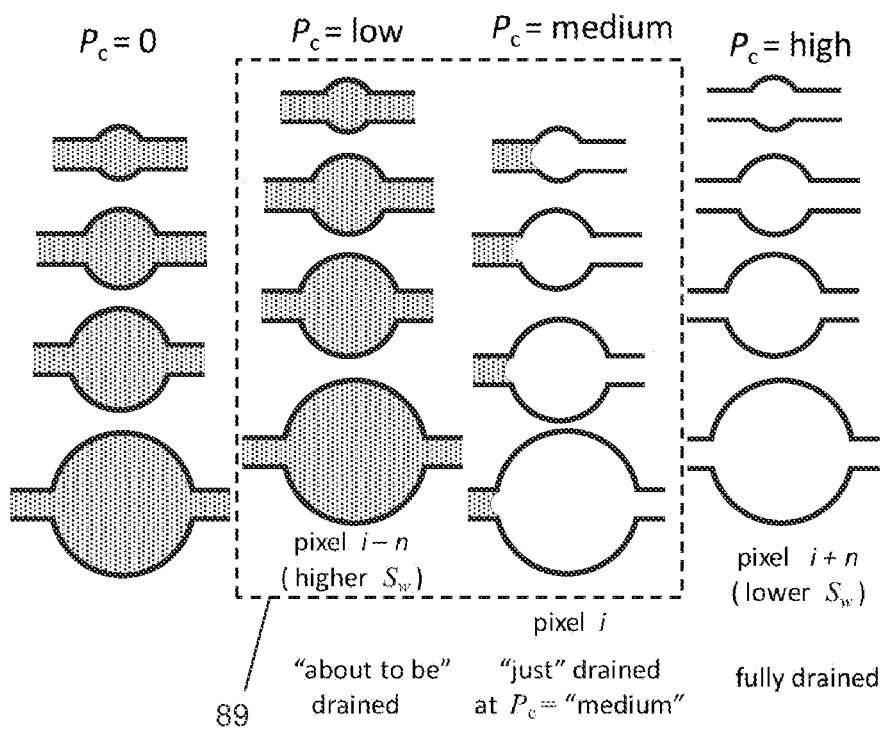

This is illustrated in diagrammatic form by FIGS. 19-21. FIG. 19 schematically shows pores of differing body and throat sizes where there is a good correlation between body size and throat size. The filled pores are illustrated by the left hand column of this diagram. Three pixels of the magnetic resonance image designated as i−n, i and i+n are shown in further columns of the diagram. As explained earlier, these correspond to different radial distances from the centrifuge axis so are subject to different pressures during centrifugation. The pixels are denoted as $P_c$=lower, medium and higher respectively. As shown, the pores drain progressively from large to small, because pore body" and pore throat sizes are well-correlated. The differential method of calculation described above compares pores in the dashed rectangle 81 and provides a better estimator of body size in pores which have "just drained" than the average size indicated by $T_{2LM}^{(i)}$ which relates to pores in the dashed rectangle 83.

FIG. 20 is similar in layout but shows pores where the same body size has various throat sizes. Consequently pores of the same body size drain at different capillary pressures. The average saturated body size indicated by $T_{2LM}^{(i)}$ relates to pores in the dashed rectangle 85 and may include pore bodies both smaller and larger than the pore body size which has "just drained," The differential method of calculation compares pores in the dashed rectangle 87 and provides a better estimator of the "just drained" body size.

FIG. 21 is again similar in layout to FIG. 19. It shows pores of differing body size but an equal throat size. The differential method of calculation compares pores in the dashed rectangle 89 and always reflects the average body size of pores which have "just drained" at capillary pressure $p_c$, irrespective of correlation with throat size. The average saturated body size indicated by $T_{2LM}^{(i)}$ is not shown in this FIG. 21 because the contributing pores all have smaller throats than those shown.

Figure 25:
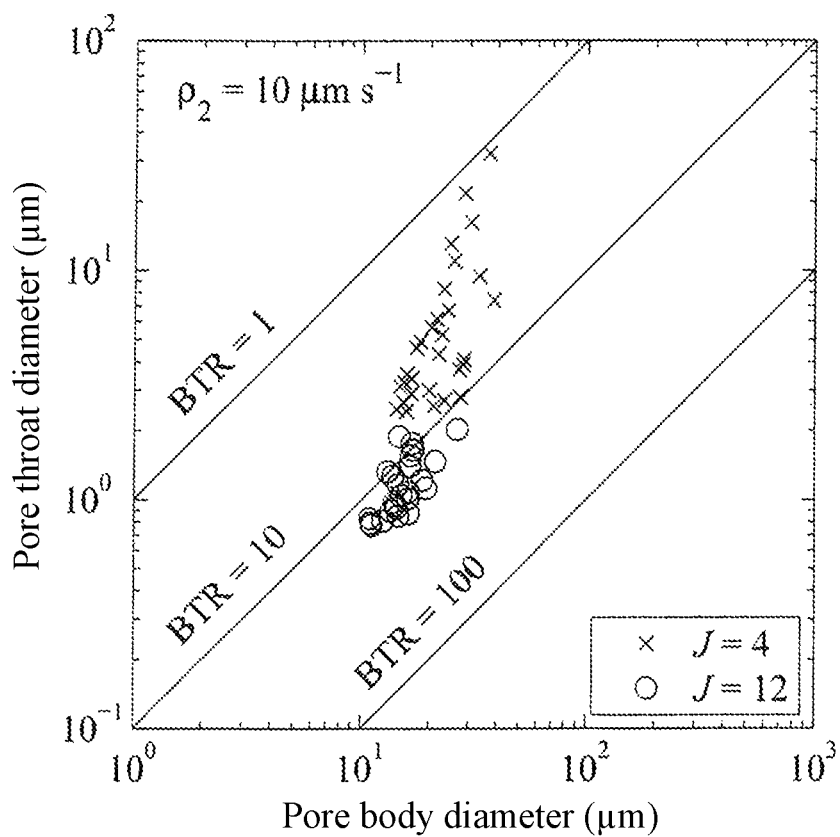
FIG. 25 is a plot of pore throat diameter against associated pore body size in Berea sandstone.

Example results for this differential method of calculation described above are shown in FIGS. 23 and 25 which are plots of "average pore body size $\langle d_b \rangle$ for pores which are adjacent the drainage boundary and so have "just drained" against throat size for the same pores. These plots in FIGS. 23 and 25 are for Estaillades limestone and Berea sandstone respectively.

Figure 23:
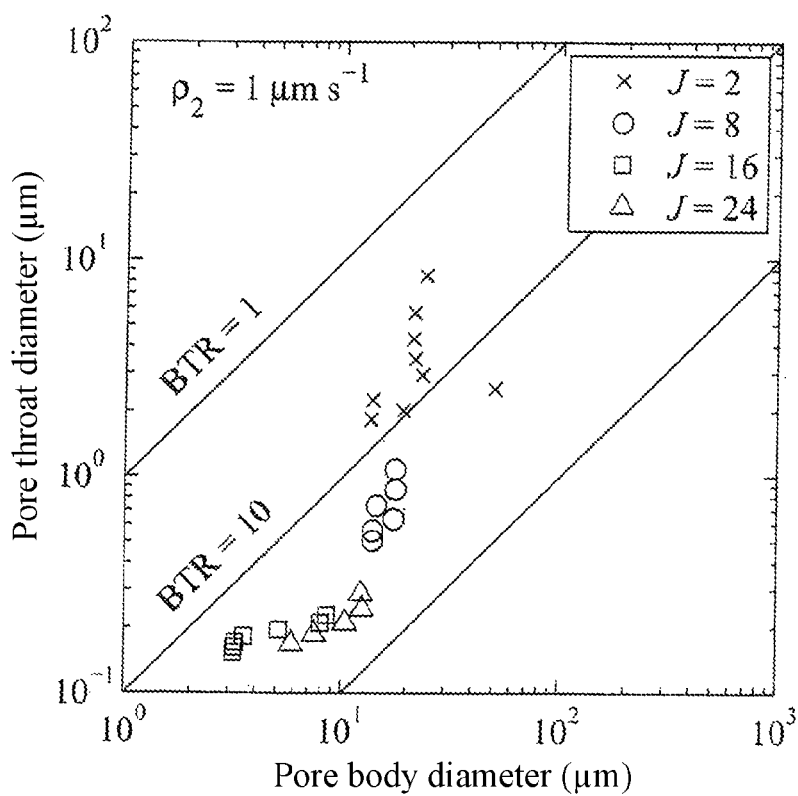
FIG. 23 is a plot of pore throat diameter against associated pore body size in Estaillades limestone.

It can be seen that FIG. 23 differs from FIG. 22 described earlier, thus showing that these two interpretations of data for the same Estaillades limestone lead to different end results. By contrast there is less difference between FIGS. 24 and 25 for Berea sandstone.

The above discussion has envisaged centrifuging a sample saturated with brine to force drainage of the brine which is then replaced by air. Magnetic resonance observes the $^1H$ nuclei (protons) in the brine. Any magnetic resonance signal from $^1H$ nuclei in the air which replaces the brine is of low intensity and will be effectively invisible. It would be possible to carry out experiments with the converse arrangement in which a liquid is imbibed and replaces air rather than drained. Discussion and formulae generally as above would apply.

Two Liquids

Determination of the distribution of a magnetic resonance parameter as well as distribution of liquid in a sample is also useful for experiments where centrifuging causes forced drainage of one liquid and forced imbibition of another. In this event it is necessary to distinguish the two liquids. There are some known possibilities for obtaining an MRI profile for one liquid in such circumstances.

One well known possibility is to use $D_2O$ or a solution of a salt in $D_2O$ as one liquid while using hydrocarbon as the other liquid. It is better to use a simple alkane such as decane rather than crude oil as the hydrocarbon because acidic atoms in crude oil can migrate into $D_2O$ reducing the distinction between the two liquids.

Another known possibility, which does not require $D_2O$ and which has been proposed in U.S. Pat. No. 6,178,807, is to use a hydrocarbon such as hexadecane which melts slightly above room temperature. Centrifuging is carried out at a mildly elevated temperature at which the hydrocarbon is liquid, but the centrifuged sample is cooled to freeze the hydrocarbon to a solid state before observation of magnetic resonance. $T_2$ for the hydrocarbon is then reduced to a short value characteristic of a solid and is not observed by the methods used here to observe $T_2$ of liquids. Thus the hydrocarbon becomes invisible to NMR once it has solidified.

In some embodiments of the present disclosure, observation of $T_2$ is used to distinguish between an aqueous liquid and a hydrocarbon which is also liquid. This can be achieved by adding paramagnetic cations which shorten $T_2$ of the aqueous liquid. As a demonstration, a sample of Bentheimer sandstone with dimensions 60 mm length×38 mm diameter was saturated with dodecane. Known volumes of 2 wt. % KCl brine were imbibed into the sample and $T_2$ maps were acquired after imbibition. The brine was doped with MnEDTA to provide $T_2$ contrast relative to the dodecane.

Figure 26:
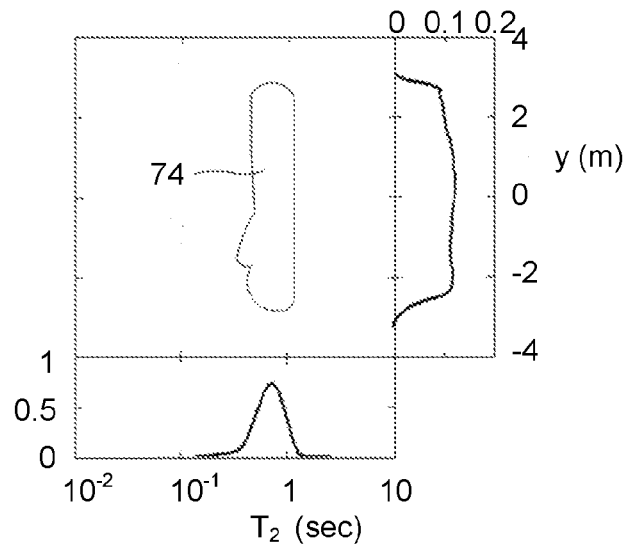
FIG. 26 is a map of magnetic resonance signal against position and $T_2$ observed with Bentheimer sandstone saturated with dodecane.
Figure 27:
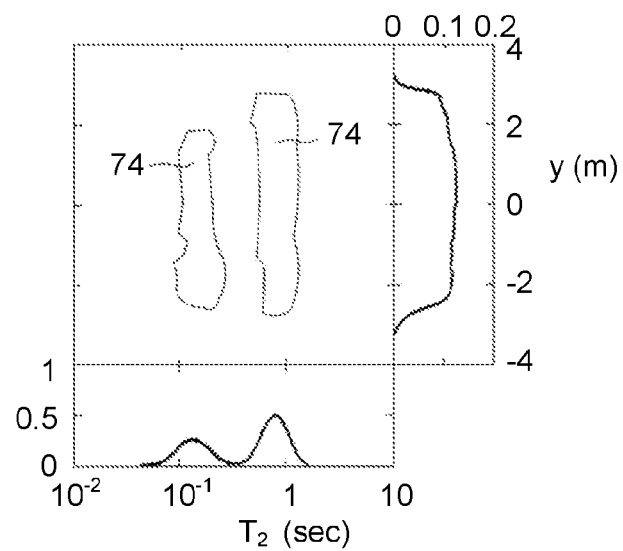
FIGS. 27 and 28 are corresponding maps when the Bentheimer sandstone sample has imbibed brine containing paramagnetic ions.
Figure 28:
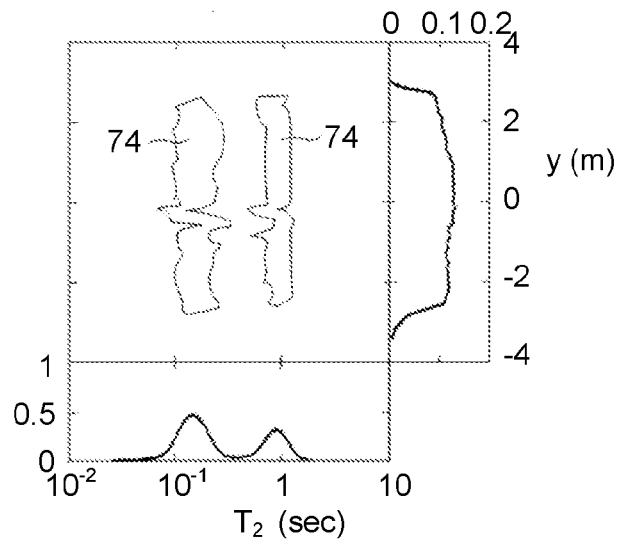

A schematic illustration of the $T_2$ map for the original, dodecane saturated sample is shown in FIG. 26 and shows that the sample was saturated uniformly along its length. The original map showed signal intensity as a grey scale, but here the area of high signal intensity is outlined and indicated 74. Corresponding illustrations of the $T_2$ maps after imbibition of 3 cm$^3$ and 15 cm$^3$ brine are shown in FIGS. 27 and 28. The $Mn^{2+}$ doped brine seen in these FIGS. 27 and 28 has a distinctively shorter range of $T_2$ and enables MR profiles for each liquid to be extracted from the observed magnetic resonance data After 3 cm$^3$ of brine had been imbibed, FIG. 23 shows that the brine (short $T_2$) can be seen extending from the inlet end of the sample and the brine saturation decreases towards the outlet end of the sample. The oil saturation shows the opposite trend. The sample remains at a uniform saturation state overall. After 15 cm$^3$ of brine had been imbibed, FIG. 24 shows that both the brine and dodecane are seen to be distributed uniformly throughout the sample. This suggests the brine has fingered through the dodecane and has failed to displace all of the oil.

If a hydrogen index (i.e., MR signal units per gram of liquid) is obtained for the brine and also for the dodecane, the oil and brine volumes can be calculated from the magnetic resonance signal intensities.

In some embodiments of the present disclosure, measurements of more than one of the magnetic resonance parameters $T_1$, $T_2$ and D are obtained, and the correlation of these parameters is further correlated with the longitudinal position along the sample. Correlations of $T_1$ and $T_2$ and correlations of D and $T_2$ are already known in the field of NMR, but further correlation with spatial position after centrifuging is a novel development.

Figure 29:
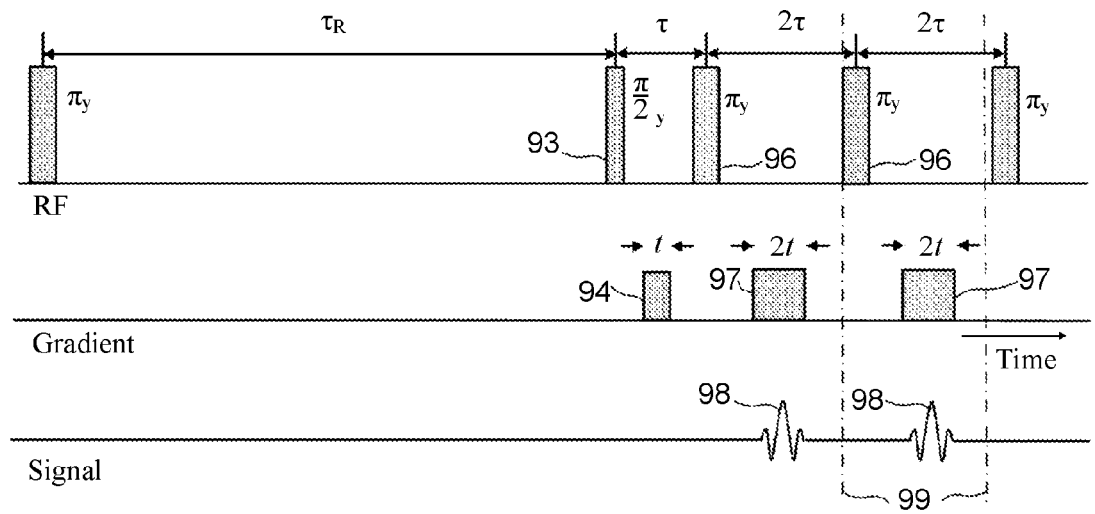
FIG. 29 is a diagram of pulse sequences and applications of magnetic field gradient used to obtain correlations of $T_1$, $T_2$ and position.

FIG. 29 shows a sequence of radiofrequency pulses and periods of gradient coil energization which can be used to obtain a spatially resolved correlation of $T_1$ and $T_2$. The pulse sequence is similar to a sequence shown as FIG. 1(c) in M. D. Hürlimann and L. Venkataramanan, "Quantitative measurement of two-dimensional distribution functions of diffusion and relaxation in grossly inhomogeneous fields," J. Magn. Reson., Vol. 157, pp. 31-42, 2002. It includes a CPMG radiofrequency pulse sequence beginning with a 90° pulse 93. Spatial resolution is obtained by energizing gradient coils, as shown by the second line of the diagram, to superimpose a magnetic field gradient on the main magnetic field. The radiofrequency pulse 93 is followed by application of a magnetic field gradient for time t as indicated at 94. This is followed by a sequence which is applying a 180° refocusing pulse 96 without the magnetic field gradient, applying the magnetic field gradient for a time 2t as indicated at 97 and recording the emitted signal 98 while the field gradient is being applied. This sequence is repeated many times. The steps of one repeat are enclosed between the dotted lines 99.

Figure 30:
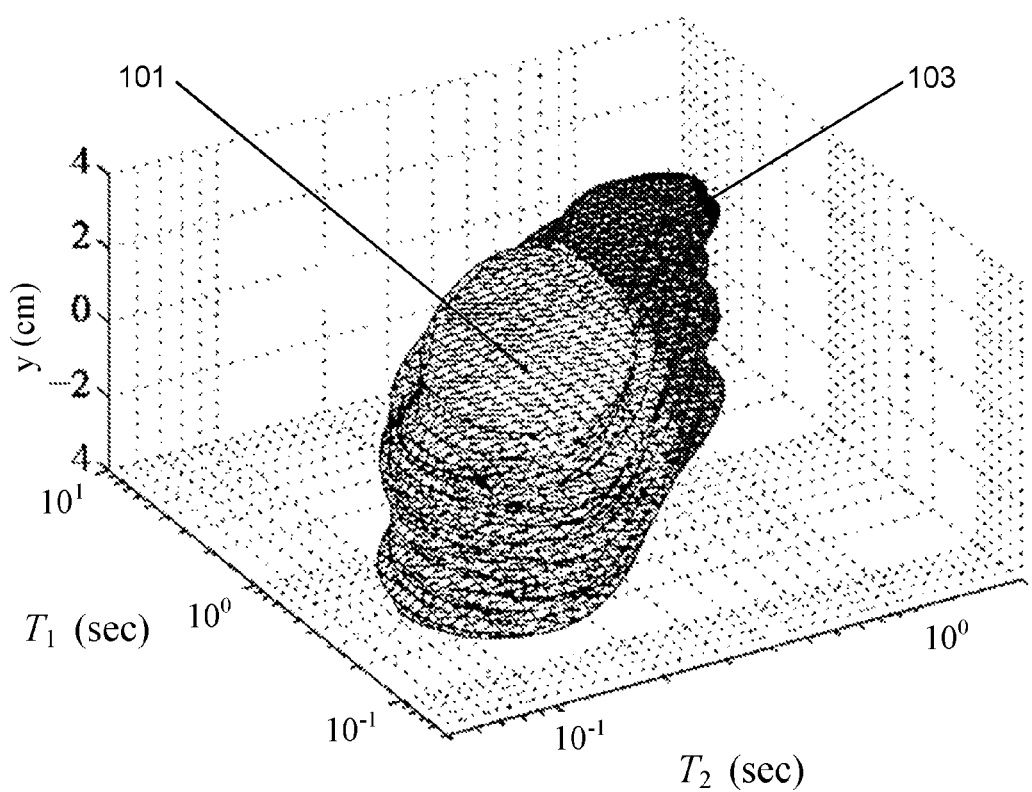
FIG. 30 is a three axis plot of data obtained with the Bentheimer sandstone of FIG. 28 and the sequences of FIG. 29.

FIG. 30 shows a three dimensional plot of $T_1$, $T_2$ and position y obtained using the pulse sequence of FIG. 29 to examine the Bentheimer sandstone sample which had imbibed 15 cm$^3$ brine. Data points for the MnEDTA doped brine appear as a network 101. Data points for dodecane appear as a darker colored network 103. The data can be used to provide a plot of the ratio of $T_1/T_2$ against position y, which provides an indication of adsorbate/adsorbent interaction strength and can be used as a qualitative estimate of wettability, as has been disclosed for whole samples by McDonald et al., "Surface relaxation and chemical exchange in hydrating cement pastes: A two-dimensional NMR relaxation study," Phys. Rev. E, Vol. 72, p. 011409, 2005, by Mitchell et al., "A rapid measurement of: The DECPMG sequence," J. Magn. Reson., Vol. 200, pp. 198-206, 2009 and by Weber et al.: "Comparing strengths of surface interactions for reactants and solvents in porous catalysts using two-dimensional NMR relaxation correlations," J. Phys. Chem. C, Vol. 113, pp. 6610-6615, 2009.

Figure 31:
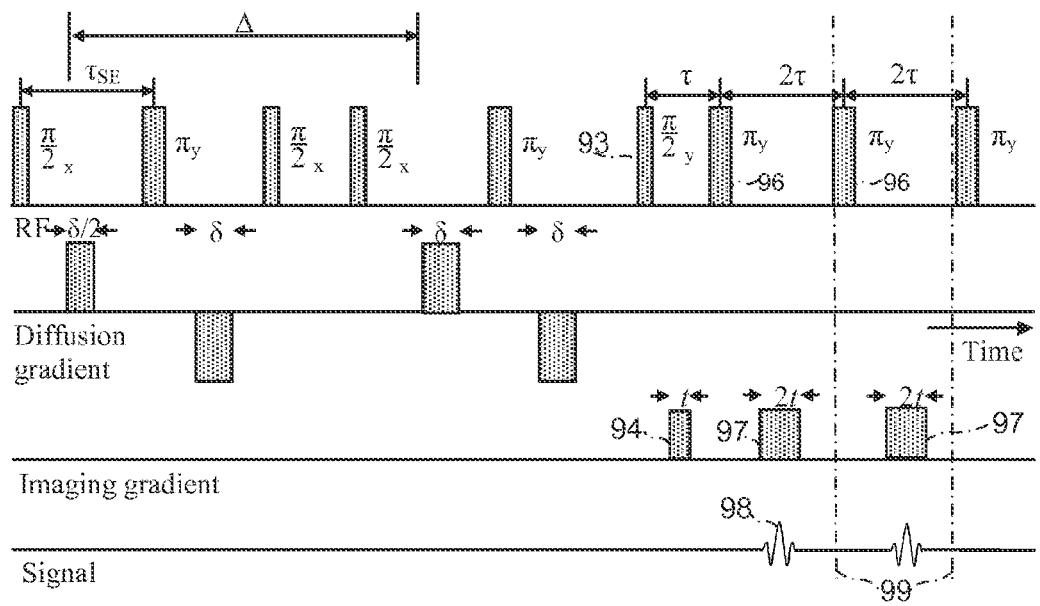
FIGS. 31 and 32 are diagrams of two pulse sequences and applications of magnetic field gradient used to obtain correlations of $T_2$, D and position.

FIG. 31 shows a sequence of radiofrequency pulses and periods of gradient coil energization which can be used to obtain a spatially resolved correlation of $T_2$ and D. The first part of the sequence is similar to a sequence disclosed in Cotts et al.: "Pulsed field gradient stimulated echo methods for improved NMR diffusion measurements in heterogeneous systems," J. Magn. Reson., Vol. 83, pp. 252-266, 1989. This is followed by a CPMG pulse sequence during which the application of magnetic field gradients as shown in the third line of the diagram labelled "imaging gradient" makes it possible to correlate additionally with the position along the length of the sample. As shown on the third line, the magnetic field gradients applied during the CPMG radiofrequency pulse sequence may be of less magnitude than those on the second line of the diagram labelled "diffusion gradient." The CPMG sequence and the accompanying magnetic field gradients are as shown in FIG. 29 and the same reference numerals are used.

Figure 32:
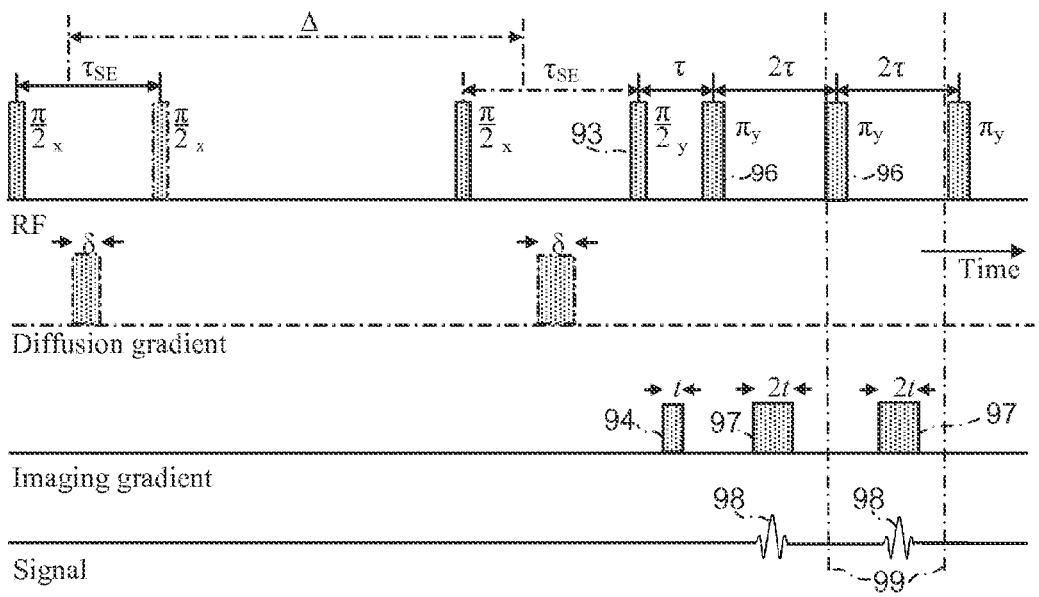

FIG. 32 shows another sequence of pulses and periods of gradient coil energization which can be used to obtain a spatially resolved correlation of $T_2$ and D. The first part of the pulse sequence is similar to a sequence disclosed in E. O. Stejskal and J. E. Tanner, "Spin diffusion measurements: Spin echoes in the presence of a time-dependent field gradient.," J. Chem. Phys., Vol. 42, pp. 288-292, 1965. Once again there is a CPMG sequence of radio frequency pulses and accompanying magnetic field gradients as in FIG. 29 and the same reference numerals are used.

It will be appreciated that the example embodiments described in detail above can be modified and varied within the scope of the concepts which they exemplify. Features referred to above or shown in individual embodiments above may be used together in any combination as well as those which have been shown and described specifically. Accordingly, all such modifications are intended to be included within the scope of this disclosure as defined in the following claims.

The invention claimed is:

1. A method of analysing properties of a porous sample, comprising:
   centrifuging the sample while it contains at least one liquid,
   determining a distribution of at least one liquid in the sample, relative to the direction of centripetal acceleration by the centrifuge, by magnetic resonance imaging of the sample,
   determining a distribution of at least one magnetic resonance parameter, relative to the direction of centripetal acceleration by the centrifuge, where the parameter is one of longitudinal relaxation time $T_1$, transverse relaxation time $T_2$ and diffusion coefficient D;
   distinguishing a portion of the porosity of the sample by a range of values of said at least one magnetic resonance parameter; and
   determining the distribution of said at least one liquid relative to the direction of centripetal acceleration by the centrifuge, in the said portion of the porosity of the sample.

2. A method according to claim 1 further comprising determining a capillary pressure curve from the distribution of at least one liquid in the sample.

3. A method according to claim 1 further comprising determining a capillary pressure curve from the distribution of at least one liquid in the said portion of the porosity of the sample.

4. A method according to claim 1 wherein the magnetic resonance parameter is transverse relaxation time $T_2$.

5. A method according to claim 4 wherein determining the distribution of transverse relaxation time $T_2$ is done by means of a frequency encoded method comprising:
   placing the sample in a magnetic field;
   applying a 90° radiofrequency pulse to the sample;
   superimposing a magnetic field gradient on the magnetic field;
   observing echo signals by a sequence of removing the superimposed magnetic field gradient, applying a 180° refocusing pulse, then again superimposing a magnetic field gradient on the magnetic field and observing the radiofrequency emitted from the sample over a range of frequencies while the magnetic field gradient is applied;

repeating the said sequence multiple times; and calculating values correlating radiofrequency signal strength with $T_2$ at positions distributed within the sample.

6. A method according to claim 1 wherein centrifuging causes expulsion of said one liquid and replacement of the expelled liquid with gas.

7. A method according to claim 1 wherein centrifuging causes expulsion of one liquid and imbibition of another liquid, wherein one of the liquids is hydrocarbon and the other of them is an aqueous solution.

8. A method according to claim 7 wherein the aqueous solution contains paramagnetic cations.

9. A method according to claim 7 comprising determining a distribution of one of the two liquids relative to the direction of centripetal acceleration by the centrifuge.

10. A method according to claim 1 wherein said at least one magnetic resonance parameter comprises both the parameter of longitudinal relaxation time $T_1$ and the parameter of transverse relaxation time $T_2$.

11. A method according to claim 1 wherein said at least one magnetic resonance parameter comprises both the parameter of transverse relaxation time $T_2$ and the parameter of diffusion coefficient D.

12. A method of analysing properties of a porous sample, comprising:

centrifuging the sample while it contains at least one liquid;

determining a distribution of at least one liquid in the sample, relative to the direction of centripetal acceleration by the centrifuge, by magnetic resonance imaging of the sample;

determining pore throat sizes from the distribution of at least one liquid in the sample;

determining a distribution of at least one magnetic resonance parameter, relative to the direction of centripetal acceleration by the centrifuge, where the parameter is one of longitudinal relaxation time $T_1$, transverse relaxation time $T_2$ and diffusion coefficient D;

determining pore body sizes from the distribution of the magnetic resonance parameter; and determining relationship between pore throat sizes and pore body sizes in the sample.

13. A method according to claim 12 wherein the relationship is between individual values of pore throat size and an average of body sizes of pores having pore throat sizes no greater than the said individual value of throat size.

14. A method according to claim 12 wherein the relationship is between individual values of pore throat size and an average of body sizes of pores having the said individual pore throat size.

15. A method of analysing properties of a porous sample, comprising:

centrifuging the sample while it contains at least one liquid, determining a distribution of at least one liquid in the sample, relative to the direction of centripetal acceleration by the centrifuge, by magnetic resonance imaging of the sample, determining a distribution of transverse relaxation time $T_2$ relative to the direction of centripetal acceleration by the centrifuge.

16. A method according to claim 15 wherein determining the distribution of transverse relaxation time $T_2$ is done by means of a frequency encoded method comprising:

placing the sample in a magnetic field;

applying a 90° radiofrequency pulse to the sample;

superimposing a magnetic field gradient on the magnetic field;

observing echo signals by a sequence of removing the superimposed magnetic field gradient, applying a 180° refocusing pulse, then again superimposing a magnetic field gradient on the magnetic field and observing the radiofrequency emitted from the sample over a range of frequencies while the magnetic field gradient is applied;

repeating the said sequence multiple times; and calculating values correlating radiofrequency signal strength with $T_2$ at positions distributed within the sample.

17. A method according to claim 15 which also comprises determining the distribution of diffusion coefficient D relative to the direction of centripetal acceleration by the centrifuge.

* * * * *